United States Patent
Schoebinger et al.

(10) Patent No.: US 12,027,253 B2
(45) Date of Patent: Jul. 2, 2024

(54) COMPUTER-IMPLEMENTED METHODS AND EVALUATION SYSTEMS FOR EVALUATING AT LEAST ONE IMAGE DATA SET OF AN IMAGING REGION OF A PATIENT, COMPUTER PROGRAMS AND ELECTRONICALLY READABLE STORAGE MEDIUMS

(71) Applicant: Siemens Healthcare GmbH, Erlangen (DE)

(72) Inventors: Max Schoebinger, Hirschaid (DE); Michael Wels, Bamberg (DE); Chris Schwemmer, Forchheim (DE); Mehmet Akif Gulsun, Princeton, NJ (US); Serkan Cimen, Jersey City, NJ (US); Felix Lades, Erlangen (DE); Christian Hopfgartner, Fuerth (DE); Suha Ayman, Bengaluru (IN); Rumman Khan, Bangalore (IN); Ashish Jaiswal, Varanasi Uttar (IN)

(73) Assignee: SIEMENS HEALTHINEERS AG, Erlangen (DE)

( * ) Notice: Subject to any disclaimer, the term of this patent is extended or adjusted under 35 U.S.C. 154(b) by 240 days.

(21) Appl. No.: 17/730,617

(22) Filed: Apr. 27, 2022

(65) Prior Publication Data
US 2022/0351833 A1 Nov. 3, 2022

(30) Foreign Application Priority Data

Apr. 30, 2021 (EP) .................................... 21171600
Sep. 3, 2021 (EP) .................................... 21194933

(51) Int. Cl.
*G16H 30/20* (2018.01)
*G06N 5/04* (2023.01)

(52) U.S. Cl.
CPC ............... *G16H 30/20* (2018.01); *G06N 5/04* (2013.01)

(58) Field of Classification Search
CPC .................................. G16H 30/20; G06N 5/04
See application file for complete search history.

(56) References Cited

U.S. PATENT DOCUMENTS

| | | | |
|---|---|---|---|
| 8,532,360 B2 * | 9/2013 | Suri ...................... | A61B 8/483 600/410 |
| 9,349,178 B1 * | 5/2016 | Itu ........................ | A61B 6/5217 |
| 9,881,372 B2 | 1/2018 | Gulsun et al. | |
| 9,918,690 B2 * | 3/2018 | Itu ........................... | G06F 18/22 |
| 9,965,891 B2 * | 5/2018 | Grady .................... | G06T 7/174 |
| 10,111,636 B2 * | 10/2018 | Itu .............................. | G06T 7/11 |

(Continued)

FOREIGN PATENT DOCUMENTS

EP   3828836 A1   6/2021

OTHER PUBLICATIONS

Lupascu, 2013, Elsevier, pp. 1164-1180.*

(Continued)

*Primary Examiner* — Michael I Ezewoko
(74) *Attorney, Agent, or Firm* — Harness, Dickey & Pierce, P.L.C.

(57) ABSTRACT

At least one example embodiment provides a computer-implemented method for evaluating at least one image data set of an imaging region of a patient, wherein at least one evaluation information describing at least one medical condition in an anatomical structure of the imaging region is determined.

16 Claims, 6 Drawing Sheets

(56) References Cited

U.S. PATENT DOCUMENTS

| | | | |
|---|---|---|---|
| 10,176,896 B2* | 1/2019 | Sharma | G06N 20/00 |
| 10,192,640 B2* | 1/2019 | Itu | G16H 50/70 |
| 10,206,646 B2 | 2/2019 | Gulsun et al. | |
| 10,210,612 B2 | 2/2019 | Gulsun et al. | |
| 10,776,988 B2* | 9/2020 | Grady | G06T 7/337 |
| 10,966,610 B2* | 4/2021 | Gardner | A61K 38/1825 |
| 10,993,687 B2* | 5/2021 | Itu | A61B 6/504 |
| 11,210,786 B2* | 12/2021 | Min | A61B 6/504 |
| 11,232,564 B2* | 1/2022 | Min | A61B 5/7267 |
| 11,250,294 B2* | 2/2022 | Li | G06N 3/08 |
| 11,276,170 B2* | 3/2022 | Min | G06V 10/20 |
| 11,288,799 B2* | 3/2022 | Min | A61B 5/7267 |
| 11,302,001 B2* | 4/2022 | Min | A61B 5/055 |
| 11,315,247 B2* | 4/2022 | Min | G06V 10/761 |
| 11,367,190 B2* | 6/2022 | Min | A61K 49/04 |
| 11,389,130 B2* | 7/2022 | Itu | A61B 6/504 |
| 11,501,485 B2* | 11/2022 | Grady | G06T 7/337 |
| 11,690,586 B2* | 7/2023 | Min | A61B 6/5217 600/300 |
| 11,741,613 B2* | 8/2023 | Li | G06N 3/08 382/156 |
| 11,751,826 B2* | 9/2023 | Min | G06V 10/245 600/300 |
| 11,779,292 B2* | 10/2023 | Min | G06V 10/764 600/300 |
| 11,832,982 B2* | 12/2023 | Min | A61B 8/14 |
| 11,861,833 B2* | 1/2024 | Min | A61B 5/0066 |
| 2011/0257505 A1* | 10/2011 | Suri | G16H 50/30 600/443 |
| 2011/0257545 A1* | 10/2011 | Suri | A61B 8/5223 600/508 |
| 2012/0078099 A1* | 3/2012 | Suri | A61B 8/483 600/440 |
| 2016/0148371 A1* | 5/2016 | Itu | G06F 18/22 382/128 |
| 2016/0148372 A1* | 5/2016 | Itu | G06F 18/217 382/128 |
| 2016/0364859 A1 | 12/2016 | Taylor | |
| 2017/0262733 A1 | 9/2017 | Gulsun et al. | |
| 2017/0262981 A1 | 9/2017 | Gulsun et al. | |
| 2017/0296055 A1* | 10/2017 | Gardner | A61P 9/10 |
| 2017/0372475 A1 | 12/2017 | Gulsun et al. | |
| 2018/0153495 A1* | 6/2018 | Itu | A61B 5/026 |
| 2019/0038249 A1* | 2/2019 | Itu | G06F 18/2413 |
| 2019/0130578 A1 | 5/2019 | Gulsun et al. | |
| 2019/0336096 A1* | 11/2019 | Itu | G16H 50/50 |
| 2020/0226422 A1* | 7/2020 | Li | G06N 3/04 |
| 2021/0085397 A1 | 3/2021 | Passerini et al. | |
| 2021/0166342 A1 | 6/2021 | Lades et al. | |
| 2021/0212565 A1* | 7/2021 | Gardner | G01N 21/359 |
| 2021/0219935 A1* | 7/2021 | Itu | A61B 6/507 |
| 2022/0076053 A1 | 3/2022 | Gulsun et al. | |
| 2022/0092775 A1 | 3/2022 | Denzinger et al. | |
| 2022/0114388 A1* | 4/2022 | Li | G06N 3/04 |
| 2023/0148981 A1* | 5/2023 | Min | A61B 5/0075 600/300 |
| 2023/0162367 A1* | 5/2023 | Li | G06T 7/11 382/156 |
| 2023/0190224 A1* | 6/2023 | Rajguru | A61B 8/0833 600/408 |
| 2023/0394654 A1* | 12/2023 | Hampe | A61B 6/504 |
| 2023/0419487 A1* | 12/2023 | Min | A61B 5/02007 |
| 2023/0419488 A1* | 12/2023 | Min | G06T 7/62 |

OTHER PUBLICATIONS

Indraratna, 2022, Elsevier, pp. 294-302.*
Beier, 2016, Elsevier, pp. 1570-1582.*
King, 2008, pp. iv-220.*
Gharleghi, 2022, Elsevier, pp. 1-8.*
Klein et al; "Method for Automated Coronary Tree Labeling Using Bidirectional Tree structured Recurrent Neural Networks"; (2019).
Leipsic J, et al.: "SCCT guidelines for the interpretation and reporting of coronary CT angiography: a report of the Society of Cardiovascular Computed Tomography Guidelines Committee". J Cardiovasc Comput Tomogr. 2014;8(5):342-358. doi:10.1016/j.jcct.2014.07.00.
Dey D. et al.: "Artificial Intelligence in Cardiovascular Imaging: JACC State-of-the-Art Review". J Am Coll Cardiol. 2019;73(11):1317-1335. doi:10.1016/j.jacc.2018.12.054.
Cury RC et al:"Coronary Artery Disease—Reporting and Data System (CAD-RADS): An Expert Consensus Document of SCCT, ACR and NASCI: Endorsed by the ACC. JACC Cardiovasc Imaging" 2016;9(9):1099-1113. doi:10.1016/j.jcmg.2016.05.005.
Gülsün M.A., et al.: "CTA Coronary Labeling through Efficient Geodesics between Trees Using Anatomy Priors". Medical Image Computing and Computer-Assisted Intervention—MICCAI 2014. MICCAI 2014. Lecture Notes in Computer Science, vol. 8674. Springer, Cham. https://doi.org/10.1007/978-3-319-10470-6_65.
McClelland RL et al.: "Distribution of coronary artery calcium by race, gender, and age: results from the Multi-Ethnic Study of Atherosclerosis (MESA)". Circulation. 2006;113(1):30-37.
Coenen, A. et al.: "Diagnostic Accuracy of a Machine-Learning Approach to Coronary Computed Tomographic Angiography—Based Fractional Flow Reserve: Result From the MACHINE Consortium". Circulation: Cardiovascular Imaging, Am Heart Assoc, 2018, 11, e007217.
Hecht H. et al.: "Coronary Artery Calcium Data and Reporting System. An expert consensus document of the Society of Cardiovascular Computed Tomography (SCCT)", J Cardiovasc Comput Tomogr. 2018;12:185-191.
Itu, Lucian, et al. "A machine-learning approach for computation of fractional flow reserve from coronary computed tomography." Journal of Applied Physiology 121.1 (2016): 42-52.; 2016.
Mortensen MB. et al.: "CAD Severity on Cardiac CTA Identifies Patients With Most Benefit of Treating LDL Cholesterol to ACC/AHA and ESC/EAS Targets" [published online ahead of print, Jun. 17, 2020]. JACC Cardiovasc Imaging. 2020;S1936-878X(20)30322-3. doi:10.1016/j.jcmg.2020.03.017.
McCollough, Cynthia H. et al. "Coronary Artery Calcium: A Muliinstitutional, Multimanufacturer International Standard for Quantification at Cardiac CT" Radiology, vol. 243, No. 2, pp. 527-538, May 2007 // DOI: 10.1148/radiol.2432050808.
McClelland R.L. et al.: "Arterial Age as a Function of Coronary Artery Calcium (from the Multi-Ethnic Study of Atherosclerosis [MESA])", Am J Cardiol. Jan. 1, 2009; 103(1): 59-63.
Sandstedt, M. et al.: "Evaluation of an AI-based, automatic coronary artery calcium scoring software" Eur Radiol 30, 1671-1678 (2020). https://doi.org/10.1007/s00330-019-06489-x.
Fischer, P. et al.: "Deep Learning Based Automated Coronary Labeling For Structured Reporting Of Coronary CT Angiography In Accordance With SCCT Guidelines" Journal of Cardiovascular Computed Tomography 14.3 (2020): S21-S22.
Gülsün M.A. et al.: Coronary Centerline Extraction via Optimal Flow Paths and CNN Path Pruning. Medical Image Computing and Computer-Assisted Intervention—MICCAI 2016. MICCAI 2016. Lecture Notes in Computer Science, vol. 9902. Springer, Cham. https://doi.org/10.1007/978-3-319-46726-9_37.

* cited by examiner

COMPUTER-IMPLEMENTED METHODS AND EVALUATION SYSTEMS FOR EVALUATING AT LEAST ONE IMAGE DATA SET OF AN IMAGING REGION OF A PATIENT, COMPUTER PROGRAMS AND ELECTRONICALLY READABLE STORAGE MEDIUMS

CROSS-REFERENCE TO RELATED APPLICATION(S)

The present application hereby claims priority under 35 U.S.C. § 119 to European patent application numbers EP 21171600.6 filed Apr. 30, 2021 and EP 21194933.4 filed Sep. 3, 2021, the entire contents of each of which are hereby incorporated herein by reference.

FIELD

Some example embodiments relate to computer-implemented methods for evaluating at least one image data set of an imaging region of a patient, wherein at least one evaluation information describing at least one medical condition in an anatomical structure of the imaging region is determined. Other example embodiments relate to evaluation systems, computer programs and electronically readable storage mediums.

BACKGROUND

Imaging techniques are nowadays often used for diagnosis, monitoring and aftercare in medicine. An image data set of an imaging region of a patient is acquired and is then evaluated regarding medical concepts, in particular pathological and other anatomical and/or physiological anomalies and features. While, in particular in the past, evaluation was often done purely manually by so-called reading, in particular by a radiologist, with the rise of the number of imaging exams and different specialized imaging techniques, the workload and complexity of the evaluation tasks increase.

Hence, the development of evaluation algorithms working on a computing device to aid medical staff in reading medical image data sets, in particular regarding diagnosis, is an active field of research. Such evaluation algorithms use input data comprising at least one image data set to generate output data describing evaluation results, in particular physical features depicted in and/or derivable from the image data set. Recently, more evaluation algorithms based on artificial intelligence have been proposed, for example comprising a neural network. Such artificial intelligence evaluation algorithms are trained using training data comprising image data sets with associated ground truths regarding the output data, for example respective annotations made in a manual evaluation by a physician.

Evaluation algorithms based on artificial intelligence, in particular deep learning techniques, are often perceived as a "black box", such that the results are in many cases not explainable and simply have to be accepted by the user. For example, if a certain disease score summarizing several aspects of a disease is provided, the factors leading to a certain result can, in particular in the case of standard deep learning, not be ascribed to certain image features of the image data set. Some disease scores proposed by organizations follow a complex scheme of their determination, which oftentimes involve the interpretation of a reading physician. Such interpretations are learned by deep learning approaches and respectively mimicked.

In an example, coronary artery disease (CAD) is caused by the build-up of plaques in the arteries supplying the muscles of the heart, that is, the arteries in the so-called coronary artery tree. These plaques lead to a reduction in blood flow, which in turn can lead to stable or unstable angina, myocardial infarction, or sudden cardiac death, in particular in the case of a plaque rupture. In 2015, CAD affected 110 million people and resulted in 8.9 million deaths, which makes it one of the most common causes of death globally.

The recently updated National Institute of Health Care Excellence (NICE) and European Society of Cardiology (ESC) guidelines recommend cardiac computed tomography (CT) for risk stratification and as first-line test to diagnose CAD in symptomatic patients with suspected CAD, in whom obstructive CAD cannot be excluded by clinical assessment alone. Furthermore, the assessment of the coronary artery calcium score with computed tomography is considered as a risk modifier in the cardiovascular risk assessment of asymptomatic subjects and recommended as such by the American Heart Association (AHA) guideline on the management of blood cholesterol.

Hence, coronary computed tomography angiography (CCTA) scans and calcium scoring (CaSc) scans are widely used in the routine assessment of patients with low to intermediate pretest probability of coronary artery disease. Due to the newly released guidelines, this trend will continue, and it is expected that the number of CCTA and CaSc examinations will continue to rise. The increase in imaging exams leads to increased demands for the reading of the image data sets acquired in these scans. Thus, solutions are required that increase efficiency during reading and reporting of such examinations and yet provide a comprehensible assessment of the general disease grade of the patient aiding in the diagnosis and in particular in decisions regarding further treatment.

Until now, the diagnostic workup of CCTA and CaSc scans is typically done manually, either by directly assessing the axial slices of the image data sets or by making use of dedicated interactive software solutions. For CCTA evaluation, the reader typically evaluates the three main coronary arteries and their side branches separately for any visually perceivable sign of disease. Signs of disease may be a narrowing of the lumen or a widening of the outer wall of the vessel. The vessel wall itself may include bright structures (calcifications), darker structures (soft plaques) and mixtures of both (mixed plaques). The severity of disease is typically evaluated by measuring the narrowing of the vessel lumen by computing the stenosis grade quantitatively and qualitatively. Plaques may further be associated with high risk plaque features like napkin ring signs, positive remodeling, spotty calcification or low attenuation. The identified findings are then described in free text form, or as structured information in the report. To standardize reporting, various reporting schemes have been proposed. Most commonly used is the 17-segment model of the American Heart Association (AHA), which has been extended to 18 segments by the Society of Cardiovascular Computed Tomography (SCCT). Finally, the extent of disease is summarized on patient level by a standardized evaluation information like "one vessel disease", "two vessel disease", or "three vessel disease" or by using the recently released CAD-RADS reporting scheme, see R. C. Cury et al., "Coronary Artery Disease—Reporting and Data System (CAD-RADS): An Expert Consensus Document of SCCT, ACR and NASCI: Endorsed by the ACC", JACC Cardiovasc. Imaging 9 (2016), pages 1099-1113.

For CaSc scan evaluation, typically the total and the vessel-specific "Agatston Score" is reported, which is a measure of the amount of calcification present in the individual subtrees and the whole coronary tree, see C. H. McCollough et al., "Coronary artery calcium: a multi-institutional, multimanufacturer international standard for quantification at cardiac CT", Radiology 243(2007), pages 527-538.

The evaluation of the image data sets of both scans is typically performed using postprocessing software that supports the reading by preparing suitable views fully automatically. For CCTA evaluation, the major coronary arteries are identified automatically and displayed as Curved Planar Reformations (CPRs), which allow to evaluate the whole vessel course in a single view. For CaSc evaluation, the native CT image data set is being thresholded and calcification candidates are highlighted. The user then clicks onto the candidates to confirm or reject them, and to assign them to the individual subtrees.

In any case, these procedures are user-driven, interactive, and time consuming. In clinical routine, users spend a considerable amount of time for documenting obvious findings, leaving less time for the actual interpretation of the more complicated conditions.

As already mentioned above, ongoing research focuses on evaluation algorithms that relieve the user of this burden by using artificial intelligence (AI) to automate the detection and classification of diseases, including the exemplarily discussed coronary artery disease. Evaluation algorithms trained using machine learning may also be called trained evaluation functions. An overview of this field of research with focus on cardiovascular imaging is given in an article by D. Dey et al., "Artificial Intelligence in Cardiovascular Imaging: JACC State-of-the-Art Review", J. Am. Coll. Cardiol. 73(2019), pages 1317-1335.

SUMMARY

Regarding the resulting evaluation information, the user may not be able to understand how the evaluation system arrived at its conclusions. In particular, the user cannot interact with the evaluation system such that assessment of certain features may be consistently modified.

At least one example embodiment provides a computer-implemented evaluation method and evaluation system that provides summarizing evaluation information in an automatic, yet understandable manner and in particular allows consistent, interactive modification of the automatically derived assessment.

This object is achieved by providing a computer-implemented method, evaluation system, computer program and electronically readable storage medium according to the independent claims. Advantageous embodiments are described by the dependent claims.

According to at least one example embodiment a computer-implemented method for evaluating at least one image data set of an imaging region of a patient, wherein at least one evaluation information describing at least one medical condition in an anatomical structure of the imaging region is determined, wherein the method comprises segmenting and labelling the anatomical structure using at least one first evaluation algorithm to generate at least one first evaluation data set and entering the at least one first evaluation data set into an evaluation database; determining at least one second evaluation data set describing at least one local medical feature in the anatomical structure using at least one second evaluation algorithm and entering the at least one second evaluation data set into the evaluation database; determining the at least one evaluation information by applying inference rules of a rule set, wherein each inference rule derives at least one result evaluation data set from at least one input evaluation data sets and wherein the evaluation database is augmented by adding the result evaluation data sets for each rule application linked to the respective input evaluation data sets in the evaluation database; and outputting an interactive presentation comprising information from at least a part of the evaluation data sets of the evaluation database, wherein the initially displayed interactive presentation comprises at least one of the at least one evaluation information and, when a user interaction command related to at least one chosen result evaluation data set is received, updating the interactive presentation to include information of at least one input evaluation data set from which the chosen result evaluation data set is derived.

According to at least one example embodiment, the interactive presentation comprises (i) at least one of image data from the image data set, (ii) visualization data derived from at least one of the at least one image data set or from at least one evaluation data set, or (iii) at least one overview image.

According to at least one example embodiment, at least a part of the information from the evaluation data sets included in the interactive presentation is presented by at least one of annotating presented image data, overlaying the presented image data, modifying the presented image data or visualization data.

According to at least one example embodiment, at least one evaluation data set is modified based on received user input, wherein all evaluation data sets linked to the modified evaluation data sets in the evaluation database are at least one of (i) marked, (ii) all result evaluation data sets derived using the modified evaluation data sets are updated using the respective inference rules, (iii) at least a part of at least one evaluation data set or sets from which a modified evaluation data set was derived is marked as less reliable, or (iv) excluded from the interactive presentation.

According to at least one example embodiment, the anatomical structure is hierarchically divided into segments in multiple hierarchy levels, wherein at least a part of the result data sets (i) is determined for a defined hierarchy level or (ii) comprises evaluation data relating to a defined segment.

According to at least one example embodiment, the rules set comprises at least one of (i) inference rules for deriving lowest hierarchy level result evaluation data sets from at least one of the at least one second evaluation data sets, respectively, or (ii) inference rules deriving a higher hierarchy level result evaluation data set from at least one lower hierarchy level input evaluation data set.

According to at least one example embodiment, at least one of additional patient data or statistical data are received, wherein information from at least one of the additional patient data or statistical data is used by at least one inference rule.

According to at least one example embodiment, if a finalizing user command is received, a combination data set comprising at least one of the at least one image data set or at least a part of the evaluation data of the evaluation data sets, is compiled and provided for storing.

According to at least one example embodiment, the method includes deciding, in which, before applying any first or second evaluation algorithm, the at least one image data set is analyzed regarding (i) suitability for at least one of the first evaluation algorithm or the second evaluation algorithm, (ii) to determine at least one of a suitable first evaluation algorithm or a suitable second evaluation algorithm, or (iii) if multiple image data sets are received, associate image data sets to sets of the at least one of the first evaluation algorithm or the second evaluation algorithm.

According to at least one example embodiment, the anatomical structure is a coronary artery tree, wherein at least one coronary computed tomography angiography scan and at least one calcium scoring computed tomography scan are received as image data sets and the evaluation information comprises at least one atherosclerotic disease-related score and at least one calcium score for the patient.

According to at least one example embodiment, as a preprocessing step, the cardiac-gated coronary computed tomography angiography scan is split into several image data sets according to multiple phases of the heart cycle, wherein at least one of (i) the image data set of a predefined heart phase is selected for evaluation or (ii) at least one of the image data set or a subset of the at least one image data set best meeting requirements of at least one of the first evaluation algorithm or the second evaluation algorithm is forwarded to the respective at least one of the first evaluation algorithm or the second evaluation algorithm.

According to at least one example embodiment, after the at least one first evaluation data set has been determined, which describes segments of the coronary artery tree, for at least one of at least one segment or at least one group of segments, the determination of meeting the requirements is performed on subsets only showing at least one of the segment or group, respectively.

According to at least one example embodiment, to segment and label the coronary artery tree as anatomical structure: centerlines of coronary arteries are detected by at least one of the at least one first evaluation algorithm, the coronary lumen surrounding the centerlines is detected by at least one of the at least one first evaluation algorithm, and the detected coronary arteries are classified according to at least one of a predefined classification scheme or a user-selectable classification scheme of the coronary artery tree into segments for labelling by at least one of the at least one first evaluation algorithm, such that the at least one first evaluation data set describes, for each point in the coronary artery tree, to which segment the point belongs, the local course of the segment and the local shape of the segment.

According to at least one example embodiment, the at least one second evaluation algorithm detects and analyzes lesions in the coronary artery tree such that a second evaluation data set is generated for each lesion, comprising at least one information chosen from the group comprising: a start position and end position of the lesion, a plaque class, a plaque vulnerability information derived from or describing the presence of at least one vulnerability indicator, positive remodeling, spotty calcification, and napkin ring signs, or a stenting information describing the presence of a stent from an earlier intervention.

According to at least one example embodiment, the inference rules derive result evaluation data from at least one of the first evaluation data set or the second evaluation data set for three hierarchy levels, the three hierarchy levels including a lesion level relating to single lesions, a segment level relating to single segments of coronary arteries, and a patient level relating to the whole coronary artery tree.

According to at least one example embodiment, the interactive presentation includes at least one of a coronary unfolded view, a schematic view, at least one lesion-specific view, or a percentile chart relating to at least one calcium score.

According to at least one example embodiment, an evaluation system for evaluating at least one image data set of an imaging region of a patient to determine at least one evaluation information describing at least one medical condition in an anatomical structure of the imaging region, wherein the evaluation system comprises an image interface configured to receive the at least one image data set; a storage device configured to store an evaluation database and a rule set; at least one first determination unit configured to segment and label the anatomical structure using at least one first evaluation algorithm to generate at least one first evaluation data set and determine at least one second evaluation data set describing at least one local medical feature in the anatomical structure using at least one second evaluation algorithm, wherein the at least one first determination unit is adapted to enter the at least one first and the at least one second evaluation data set into the evaluation database; a second determination unit configured to determine the at least one evaluation information by applying inference rules of the rule set, wherein each inference rule derives at least one result evaluation data set from at least one input evaluation data set, wherein the second determination unit is adapted to augment the evaluation database by adding the result evaluation data sets for each rule application linked to the respective input evaluation data sets in the evaluation database; and a user interface unit configured to output an interactive presentation comprising information from at least a part of the evaluation data sets of the evaluation database, wherein the initially displayed interactive presentation comprises at least one of the at least one evaluation information and the user interface is adapted to receive a user interaction command related to at least one chosen result evaluation data set and to update the interactive presentation to include information of at least one input evaluation data set from which the chosen result evaluation data set is derived.

According to at least one example embodiment, a computer program, when executed by a computing device of an evaluation system, is configured to cause the evaluation system to perform a method according to an example embodiment.

According to at least one example embodiment, an electronically readable storage medium having instructions, when executed by a computing device of an evaluation system, is configured to cause the evaluation system to perform a method according to an example embodiment.

According to at least one example embodiment, an evaluation system for evaluating at least one image data set of an imaging region of a patient to determine at least one evaluation information describing at least one medical condition in an anatomical structure of the imaging region, wherein the evaluation system comprises a storage device configured to store an evaluation database and a rule set; and at least one processor configured to execute computer-readable instructions to cause the evaluation system to, receive the at least one image data set, segment and label the anatomical structure using at least one first evaluation algorithm to generate at least one first evaluation data set and determine at least one second evaluation data set describing at least one local medical feature in the anatomical structure using at least one second evaluation algorithm, wherein the at least one first determination unit is adapted to enter the at least one first and the at least one second evaluation data set into the evaluation database, determine the at least one evaluation information by applying inference rules of the rule set, wherein each inference rule derives at least one result evaluation data set from at least one input evaluation data set, wherein the second determination unit is adapted to augment the evaluation database by adding the result evaluation data sets for each rule application linked to the respective input evaluation data sets in the evaluation database, and output an interactive presentation comprising information from at least a part of the evaluation data sets of the evaluation database, wherein the initially displayed interactive presentation comprises at least one of the at least one evaluation information and the user interface is adapted to receive a user interaction command related to at least one chosen result evaluation data set and to update the interactive presentation to include information of at least one input evaluation data set from which the chosen result evaluation data set is derived.

BRIEF DESCRIPTION OF THE DRAWINGS

Other objects and features of example embodiments will become apparent from the following detailed description considered in conjunction with the accompanying drawings. The drawings, however, are only principle sketches designed solely for the purpose of illustration and do not limit example embodiments. The drawings show.

DETAILED DESCRIPTION

Figure 1:
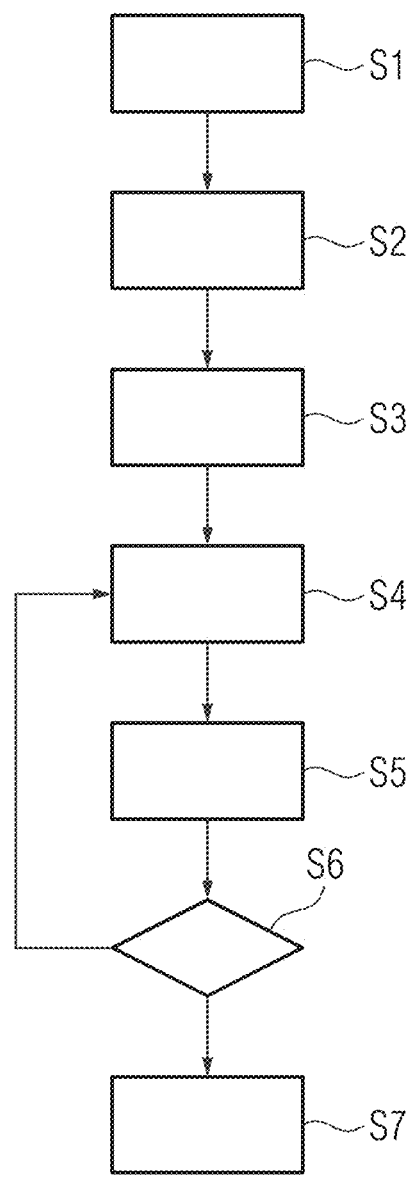
FIG. 1 a general flow chart of a method according to at least one example embodiment, FIG. 2 a principle drawing of an initial state of an interactive presentation according to at least one example embodiment, FIG. 3 a principle drawing of a second state of the interactive presentation according to at least one example embodiment, FIG. 4 a principle drawing of a third state of the interactive presentation according to at least one example embodiment, FIG. 5 a principle drawing of a fourth state of the interactive presentation according to at least one example embodiment, and FIG. 6 a schematical drawing of an evaluation system according to at least one example embodiment.

According to at least one example embodiment, a computer-implemented method for evaluating at least one image data set of an imaging region of a patient, wherein at least one evaluation information describing at least one medical condition in an anatomical structure of the imaging region is determined, comprises:
  segmenting and labelling the anatomical structure using at least one first evaluation algorithm to generate at least one first evaluation data set and entering the at least one first evaluation data set into an evaluation database,
  determining at least one second evaluation data set describing at least one local medical feature in the anatomical structure using at least one second evaluation algorithm and entering the at least one second evaluation data set into the evaluation database,
  determining the at least one evaluation information by applying inference rules of a rule set, wherein each inference rule derives at least one result evaluation data set from at least one, in particular at least two, input evaluation data sets and wherein the evaluation database is augmented by adding the result evaluation data sets for each rule application linked to the respective input evaluation data sets in the evaluation database,
  outputting an interactive presentation comprising information from at least a part of the evaluation data sets of the evaluation database, wherein the initially displayed interactive presentation comprises at least one of the at least one evaluation information and, when a user interaction command related to at least one chosen result evaluation data set is received, updating the interactive presentation to include information of at least one input evaluation data set from which the chosen result evaluation data set is derived.

The terminology used herein is for the purpose of describing particular embodiments only and is not intended to be limiting of example embodiments. As used herein, the singular forms, signified e.g. by the articles "a," "an," and "the," are intended to include the plural forms as well and vice versa, unless the context clearly indicates otherwise. As used herein, the terms "and/or" and "at least one of" include any and all combinations of one or more of the associated listed items.

In preferred embodiments, at least one of the at least one first and/or second evaluation algorithms comprises a trained evaluation function, in particular a deep neural network and/or trained by a deep learning technique.

In general, a trained function mimics cognitive functions that humans associate with other human minds. In particular, by training based on training data the trained function is able to adapt to new circumstances and to detect and extrapolate patterns.

In general, parameters of a trained function can be adapted by training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

Example embodiments, conceptually, provide an "explainable artificial intelligence (AI)" system. A combination of modern, in particular deep learning-enabled, fully automated image evaluation algorithms with the approaches of a traditional rule based expert system, which encodes domain specific inference rules and derives new knowledge from local measurements by employing an inference mechanism, is proposed.

A segmentation in at least one of the at least one image data set by at least one first evaluation algorithm provides information about the anatomy and/or other features in the at least one image data set. This allows to semantically localize further evaluation results, in particular if also labelling is provided. In preferred embodiments, deep learning based approaches may be applied to derive geometrical information concerning the anatomical structure and/or to label substructures, for example segments of a blood vessel tree, according to a labelling scheme. In embodiments, the relevant parts of the anatomy are extracted as geometrical models, which form first evaluation data in the at least one first evaluation data set. These models may then be automatically labeled, in particular using a predefined, preferred terminology, for example according to a medical or clinical standard. This facilitates that at any time the location of medical features, for example findings, can be presented and documented using the proper medical terminology.

In a further example embodiment, at least one medical, in particular clinically relevant, feature, for example a pathology and/or lesion and/or finding, is detected on a localized level. Preferably, trained deep learning second evaluation algorithms are used to detect the medical features in at least one of the at least one image data set. For each medical feature, for example, the location and further meta data, for example a characterization of a pathology, may be determined as second evaluation data. Preferably, for each such finding, that is each such medical feature, a second evaluation data set is determined and stored into the evaluation database. These second evaluation data sets, as they each refer to a single, localizable medical feature and form the basis for all further evaluation, may also be called "atomic" evaluation data sets.

In at least one example embodiment, these (usually multiple) second ("atomic") evaluation data sets together with the at least one first evaluation data sets stored in the evaluation database are seen as a knowledge base, from which further result evaluation data, which, of course, comprises the evaluation information, is derived in a rule-based diagnostic workup. To this end, the evaluation database (which can be understood as a knowledge database of an expert system) is then processed by inference rules of a rule set, which may, for example, encode logical conclusions, statistical derivations, and/or the knowledge from guidelines, as for example those issued by societies like the American Heart Association. Inference rules may, for example, comprise logical and/or statistical operations and/or basic if-then-else rules. It is also conceivable that they are at least partially based on other knowledge-based methods (e.g. machine learning-based classification).

The derived knowledge, that is result evaluation data, is added back to the evaluation database. All data sets remain linked by the respective inference rules, which in particular, as further discussed below, allows an inference mechanism to be implemented, which keeps first and second evaluation data ("atomic information") and result evaluation data ("derived information") consistent at any time.

In the next main step of the method, the results are presented to a user in an interactive presentation. The interactive presentation is constructed to be able to present all information in the evaluation database. Preferably, on initiation, the interactive presentation shows at least a part of the evaluation information as one of the major evaluation purposes. In this manner, the essential information for all detected medical features and anatomy is provided at once, for example in an overview. By interacting with the displayed interactive presentation using user interaction commands, the user can change the interactive presentation to purposefully view evaluation data of interest, in particular also evaluation data from which evaluation information was derived in the rule-based diagnostic workup.

In this manner, automated results are combined with a user interaction component which make the evaluation system's results fully traceable and comprehensible. Consistency of the evaluation results with user expectations is improved by deriving the local low-level information (second evaluation data) from deep learning-enabled second evaluation algorithms and inferring high level information using inference rules capturing domain knowledge. This combination allows to achieve the high accuracy of deep learning algorithms, while maintaining the comprehensibility and traceability of results.

The inventive approach may be employed in a large number of contexts. For example, in a computer-aided detection approach (CADe), example embodiments may be used to aid in localizing/marking regions that may reveal specific abnormalities. In a computer-aided diagnosis (CADx) usage scenario, the CADe scenario is extended by characterizing/assessing disease, disease type, severity, stage and progression. Different variations are conceivable. In a full implementation, even evaluation information-based patient management recommendations could be provided by example embodiments.

The method and/or evaluation system may be integrated into a reading workstation, for example in advanced visualization workstations for interactive reading of image data sets. In this context, the interactive reading may be expedited by providing the automatically determined evaluation information and further evaluation data, which can be taken into account by the user when assessing the image data sets, for example to provide a diagnosis.

In other embodiments, the method and/or evaluation system may also be integrated into an imaging device, for example a computed tomography scanner, providing further information already at the location of the scan. For example, basic, understandable and traceable assessments may be provided alongside an image data set.

Further, the method and/or evaluation system may be linked with advanced decision support approaches and/or may be part of a superordinate evaluation system applicable to many medical fields and/or examination purposes.

Preferably, as already laid out above, the second evaluation data set may comprise a location of the medical feature and additional meta data describing the feature, in particular a severity in the case of a pathology feature, in particular a lesion. Other meta data may comprise shape, composition and the like.

In preferred embodiments, the interactive presentation may comprise image data from the image data set and/or visualization data derived from at least one of the at least one image data set and/or from at least one evaluation data set and/or at least one overview image. In particular, at least a part of the information from the evaluation data sets included in the interactive presentation may be presented by annotating and/or overlaying and/or modifying presented image data and/or visualization data. Preferably, in particular regarding the initial display of evaluation information, an overview image of at least the anatomical structure may be generated, preferably based on at least one of the at least image data set. For example, the representative overview images may be generated providing the (essential) evaluation information for all detected anatomy and pathologies at once. Alternatively or preferably additionally, detailed images comprising image data and/or visualization data may be generated for single medical features and/or groups of medical features. For example, a detailed image may be generated, preferably from image data, for each medical feature detected by the at least one second evaluation algorithm. These detailed images may, in particular, be used to display first and/or second evaluation data. However, it is also possible to use detailed images to present intermediate evaluation data, for example result evaluation data used as input evaluation data to derive evaluation information. In especially preferred embodiments, such detailed images are displayed together with result evaluation data inferred by at least one inference rule from first and/or second evaluation data, such that the inferred measurements may be verified against the displayed information of the detailed image by a user. In this manner, for example, plausibility can be assessed.

In an especially advantageous embodiment, at least one evaluation data set, in particular a first and/or second evaluation data set, is modified based on received user input, wherein all evaluation data sets linked to the modified evaluation data set in the evaluation database are marked and/or all result evaluation data sets derived using the modified evaluation data set are updated using the respective inference rules and/or at least a part of at least one evaluation data set from which a modified evaluation data was derived is marked as less reliable and/or excluded from the interactive presentation. In a case in which the user is not satisfied with "atomic" or "derived" measurements, that is evaluation data in the evaluation database, they can manually adapt the evaluation data of at least one evaluation data set, in particular also by interacting with the interactive presentation, for example according to a user modification command. If, for example, a lesion has been classified as severe automatically, but the user comes to a different conclusion in his own assessment, they may accordingly modify this information of the evaluation data set. The same is true, for example, if a result seems implausible to the user. User input may be received and used to modify the respective evaluation data set. In other words, the evaluation database is updated. In preferred embodiments, this may lead to the inference rules automatically updating the result evaluation data set derived from the modified evaluation data set by a forward chaining mechanism. At the same time, any information that contributed to the modified evaluation data set can be marked as less reliable, in particular as outdated and/or invalid. In particular, further display of such less reliable information may be prevented. In some examples, even evaluation data that contributed to the modified evaluation data set can be corrected, if possible. In this manner, at any time, always up-to-date and correct evaluation data is shown and implausible situations are avoided. If other evaluation data sets are updated and/or marked as outdated/invalid, this may also be displayed in the interactive presentation, such that the user intuitively notices which shown information was influenced by his modification.

In concrete embodiments, the anatomical structure may be hierarchically divided into segments in multiple hierarchy levels, wherein at least a part of the result data sets is determined for a defined hierarchy level and/or comprises evaluation data relating to a defined segment. In this manner, starting from localized, single medical features in the second evaluation data sets, the evaluation data may be hierarchically organized, for example by combining evaluation data relating to medical features in single segments to new, derived evaluation data sets. In particular, second evaluation data sets may already form lowest hierarchy level datasets and/or the rules set may comprise inference rules for deriving lowest hierarchy level result evaluation data sets from at least one of the at least one second evaluation data set, respectively, and/or inference rules deriving a higher hierarchy level result evaluation data set from at least one lower, in particular adjacent hierarchy level input evaluation data set. In this manner, information may be propagated and evolved through multiple hierarchy levels, preferably finally resulting in anatomical structure-level/patient-level evaluation information. For example, at least one inference rule may combine all lower-hierarchy and/or local evaluation data for a defined segment.

Statistical combination, aggregation, pooling and the like may all be used. If, for example, the medical features are lesions, the number of lesions for a segment and/or the largest volume of a lesion for a segment may be derived by an inference rule. In another example, segment-specific scores may be calculated.

In a concrete embodiment, the anatomical structure may be a blood vessel tree, in particular a coronary artery tree. For such blood vessel trees, for example, two hierarchy levels (which come in addition to the medical feature level) can be provided, namely blood vessel segments and the whole blood vessel tree. Often, guidelines exist on how blood vessel trees may be divided into segments and how these segments should be labeled.

It is noted that such hierarchically describable anatomical structures are a particularly advantageous field to employ example embodiments. In such anatomical structures, often a large number of single medical features are taken into account to provide a general assessment for the whole anatomical structure or parts thereof. By combining information regarding single medical features in a controlled, rule-based environment to create an evaluation database, in which the basic first and second evaluation data set(s) are still retained, an expert system providing in-depth insight and understanding to a user is provided.

Preferably, additional patient data and/or statistical data may be received, wherein information from the additional patient data and/or statistical data is used by at least one inference rule. That is, the rule-based diagnostic workup of example embodiments may also join information about the patient and/or other external information to derive result evaluation information. For example, the evaluation system may be connected to at least one further, external information system, for example an electronic health record database, a radiology information system, a hospital information system, and/or a picture archiving and communication system (PACS). In this manner, all available information can be taken into account to provide high-quality evaluation results. Statistical information from an external source may, for example, also be used in an inference rule, for example to determine a percentile based on patient gender, age, mass and the like. In other words, the patient may be characterized in relation to a reference population.

It should be noted that the at least one image data set used as an input is not necessarily restricted to a single examination. In embodiments, the input data sets may comprise information derived from multiple examinations, which need not even share a common examination purpose. For example, image data sets from a time series of scans may be provided to the first and/or second evaluation algorithms. In embodiments, it may even be possible to use all image data sets of an electronic health record of a patient to derive evaluation information regarding multiple different anatomical structures and/or medical conditions.

In preferred embodiments, if a finalizing user command is received, a combination data set comprising the at least one image data set and/or at least a part of the evaluation data of the evaluation data sets, in particular at least the evaluation information, may be compiled and provided for storing. That is, once the user has reviewed, optionally modified and/or supplemented, the knowledge of the evaluation data sets, the evaluation results may be persisted and stored. While, in embodiments, the whole evaluation database may be stored as the combination data set, it is also possible to extract essential information and store it for later reference. For example, the combination data set may be distributed to at least one other system in a structured and/or pictorial format. In preferred embodiments, the combination data set may be provided in the DICOM format and/or for storage in a picture archiving and communication system (PACS). Other systems to which the combination data set may be forwarded are, for example, reporting and/or decision support systems.

It should be noted at this point that it is, in principle, also conceivable that, instead of display of the interactive presentation, the combination data set may be directly derived from the evaluation database and stored. For example, the review of the evaluation results may be manually disabled. In such a case, the method performs the whole use-case fully automatically, including the final archiving, for example in a PACS. The approval state of the combination data allows a final recipient of the evaluation results to distinguish between manually verified and fully automatically distributed evaluation results. In other words, in embodiments, the finalizing user command can be understood as expressing approval with the evaluation results in the evaluation database.

In embodiments, the method may further comprise a preparatory step, in which, before applying any first or second evaluation algorithm, the at least one image data set is analyzed regarding suitability for the first and/or second evaluation algorithms and/or to determine suitable first and/or second evaluation algorithms and/or, if multiple image data sets are received, associate image data sets to of first and/or second evaluations algorithms. In the preparatory step, image data may be mediated. Each time at least one new image data set, for example in a new DICOM study, is received, the evaluation system automatically verifies if the at least one image data set contains at least one image data set concerning the anatomical structure and/or medical condition, in other words is useful for the evaluation purpose of the concrete embodiment. If no relevant image data set is received, further processing is stopped. If multiple evaluation purposes may be served, received image data sets may be parsed and categorized according to the evaluation purposes. If multiple candidate image data sets are available for a given evaluation purpose, they may be prioritized according to specific prioritization rules. Finally, for each examination purpose, automatic processing may be triggered on at least one best suitable image data set. If example embodiments are implemented in a suitable environment, also optimized image data sets may be requested, for example, from an imaging device. In such a preparatory step, of course, meta data provided with the image data, for example in a DICOM study, may of course also be taken into account.

In concrete embodiments, for each set of first and second evaluation algorithms serving an evaluation purpose, requirement information comprising requirements regarding the quality and/or the content of image data to be evaluated is provided or determined. Each time at least one image data set of a patient is received for evaluation regarding a certain evaluation purpose, each image data set may be analyzed to determine a suitability information regarding each associated evaluation purpose, the suitability information indicating at least fulfilment or non-fulfilment of the requirements of the corresponding requirement information. Only at least one image data set whose suitability information indicates fulfilment of the requirement of the requirement information of at least one corresponding evaluation purpose, is forwarded for evaluation to the corresponding evaluation algorithms of the evaluation purpose and/or at least one user information and/or image processing action is executed for at least one evaluation purpose whose associated suitability information all indicate non-fulfilment of the requirements of the requirement information.

It is noted that, in the preparatory step, also other preparatory measures regarding the image data sets may be executed, for example applying preparatory image processing, defining and/or deriving image data sets to be actually evaluated and the like.

In a general remark, if multiple image data sets are evaluated, if they are not yet registered and/or motion-corrected, this might be also be done in a/the preparatory step. For example, in some applications, some image data sets may be better suited for segmentation and/or labelling of the anatomy, while other image data sets may be more suitable for deriving second evaluation data sets. If the respective image data sets are registered, however, location information can be transferred between them. This is also true for different image data sets evaluated by the at least one second evaluation algorithm.

In another general remark, the inference rules may not be limited to classical rule operations, but the rule set may also employ more elaborate classification and/or machine learning approaches which may also involve image-based classification. The results of such classifications are fed back to the inference mechanism in the same way as if they had been computed using regular rule-based processing.

Generally, example embodiments may also be used as a secondary or concurrent reader. In such a usage scenario, the evaluation system generates its output in parallel to the initial reading of the case by a radiologist. In this manner, the (human) reader can be supported by avoiding any false negative findings.

Example embodiments will now be further explained with respect to an especially advantageous embodiment, namely the use case of a cardiac study. In this advantageous embodiment, the anatomical structure is a coronary artery tree, wherein at least one coronary computed tomography angiography scan and at least one calcium scoring computed tomography scan are received as input data sets and the evaluation information comprises at least one atherosclerotic disease-related score and at least one calcium score for the patient. In particular, two evaluation purposes, namely atherosclerotic disease and calcium scoring, are involved, wherein the individual method steps for both evaluation processes will be mostly discussed separately in the following.

In this exemplary, advantageous embodiment, an evaluation system is provided allowing the fully automated evaluation of cardiac computed tomography scans, covering both coronary computed tomography angiography scans (CCTA scans) and calcium scoring scans (CaSc scans). This enables a more comprehensive assessment of the status of disease than with known products or algorithms. In particular, a refined categorization of severity of coronary artery disease is enabled, like, for example, proposed in an article by M. B. Mortenson et al, "CAD Severity on Cardiac CTA Identifies Patients With Most Benefit of Treating LDL Cholesterol to ACC/AHA and ESC/EAS Targets", JACC CardioVasc Imaging 2020, 51936-878X(20)30322-3.

Further, in this particular field of application, example embodiments may be used to rule out coronary artery disease, since healthy patients are effectively identified. For these patients, the time to a clinical report can potentially be reduced significantly as the end user must only confirm that no findings have been identified. Furthermore, a designated list of clinicians may be notified if cases with severe forms of disease which potentially require immediate further management, for example if a total occlusion of one of the coronary arteries is found. Cases with potentially more significant disease can be prioritized higher in the reading queue, ensuring a timely evaluation. In this manner, complication rates may be reduced.

Providing a combined system evaluating both CCTA and calcium scoring scans may be advantageous on its own. That is, a computer-implemented method for evaluating image data sets, which have been acquired in at least one coronary computed tomography angiography scan and at least one calcium scoring computed tomography scan, of an imaging region of a patient, is conceivable, wherein at least one evaluation information describing at least one medical condition in an anatomical structure, which is the coronary artery tree, of the imaging region and comprising at least one atherosclerotic disease-related score and at least one calcium score for the patient is determined, wherein the method comprises segmenting and labelling the anatomical structure using at least one first evaluation algorithm to generate at least one first evaluation data set and entering the at least one first evaluation data set into an evaluation database, determining at least one second evaluation data set describing at least one local medical feature in the anatomical structure using at least one second evaluation algorithm and entering the at least one second evaluation data set into the evaluation database, determining the at least one evaluation information by applying inference rules of a rule set, wherein each inference rule derives at least one result evaluation data set from at least one, in particular at least two, input evaluation data set and wherein the evaluation database is augmented by adding the result evaluation data set for each rule application linked to the respective at least one input evaluation data set in the evaluation database, using the evaluation database to output an interactive presentation comprising information from at least a part of the evaluation data set of the evaluation database and/or to create a combination data set comprising the image data set and/or at least a part of the evaluation data of the evaluation data sets, in particular at least the evaluation information.

In a preferred embodiment, as a prepossessing step, the cardiac-gated coronary computed tomography angiography scan is split into several image data sets according to multiple phases of the heart cycle, wherein the image data set of a predefined heart phase is selected for evaluation and/or at least one of the image data sets and/or a subset of at least one image data set best meeting requirements of at least one of the first and/or second evaluation algorithm is forwarded to the respective first and/or second evaluation algorithm. Optionally, when receiving a new DICOM study, it may be automatically verified if the examination contains at least one cardiac-gated coronary computed tomography angiography scan of the coronary arteries. If not, further processing may be stopped. If a cardiac-gated coronary computed tomography angiography scan is received, the scan may be split into the available heart phases, that is, intervals of the full heart cycle, for example 0 to 10%, 10 to 20%, and so on. Image data sets may be compiled for each heart phase, however, in preferred embodiments, only a best suitable image data set is used for further processing regarding the atherosclerotic disease. A suitability measure can be derived from the grade of fulfilment of requirements of a corresponding requirement information. Preferably, at least one requirement relates to coronary motion, such that the best suitable image data set would be the one showing the least coronary motion. While it is, in principle, conceivable to choose the best suitable heart phase and hence the best suitable image data set according to experience, for example as the heart phase closest to 70% (diastolic heart phase), it is preferred to analyze the image data sets, in particular to derive at least one quality parameter related to coronary motion. The best suitable image data set may then be chosen based on this at least one quality parameter. In embodiments, the image suitability classification may also be performed on a per-vessel or a per-segment basis in order to select the best suitable heart phase for assessing different parts of the corona arteries separately. In other words, after the at least one first evaluation data set has been determined, which describes segments of the coronary artery tree, for at least one segment and/or at least one group of segments, the determination of meeting the requirements is performed on subsets only showing the segment and/or group, respectively. These embodiments allow selecting the optimal image data for further evaluation and hence improve the quality of the evaluation results.

In a concrete embodiment, to segment and label the coronary artery tree as an anatomical structure:
- centerlines of coronary arteries may be detected by at least one of the at least one first evaluation algorithm,
- the coronary lumen surrounding the centerlines may be detected by at least one of the at least one first evaluation algorithm, and
- the detected coronary arteries may be classified according to a predefined and/or user-selectable classification scheme of the coronary artery tree into segments for labelling by at least one of the at least one first evaluation algorithm,
- such that the at least one first evaluation data set describes, for each point in the coronary artery tree, to which segment the point belongs, the local course of the segment and the local shape of the segment.

The primary goal of the coronary computed tomography angiography evaluation is to evaluate the presence of atherosclerotic disease in the coronary arteries. In a preferred embodiment, thus, anatomy modelling of the coronary arteries may be performed in three steps. In a first step, the centerlines of the coronary arteries may be detected by automatically tracing the coronary arteries in the CCTA image data set. The resulting coronary artery centerlines represent the morphology and topology of the patient-specific coronaries in a tree model. For concrete implementation of this first step, centerline tracing algorithms already known in the state of the art may also be employed here. As an example, it is referred to U.S. Pat. No. 10,210,612 B2. It is noted that, besides tracing of the contrast-enhanced coronary arteries, this exemplary approach also supports tracing across stents, chronic total occlusions, and coronary artery bypass grafts.

In a second step for anatomy modelling of the coronary arteries, the coronary lumen is detected. Based on the centerline tree and the CCTA image data, the coronary lumen may be detected, again using lumen segmentation algorithms known in the state of the art. Exemplarily, it is referred to US Patent Application US 2019/0130578 A1.

In a third step, to enable the evaluation and presentation of results using proper medical terminology, the detected coronary arteries are classified according to a standardized labelling scheme for the coronary artery segments, comprising, for example, segments like "proximal LAD (Left Anterior Descending)", "mid RCA (Right Coronary Artery)" or "Obtuse Marginal 1". For example, the labelling scheme proposed by the SSCT and American Heart Association in J. Leipsic et al., "SCCT guidelines for the interpretation and reporting of coronary CT angiography: a report of the Society of Cardiovascular Computed Tomography Guidelines Committee", J. Cardiovasc. Comput. Tomogr. 8 (2014), Pages 342-358, can be employed. Labelling algorithms already proposed in the state of the art may be used. As an example, it is referred to the article by A. Fisher et al., "Deep Learning Based Automated Coronary Labeling For Structured Reporting Of Coronary CT Angiography In Accordance With SCCT Guidelines", Journal of Cardiovascular Computed Tomography 14.3 (2020), pages 21-22, or to Paul Klein et al, "Method for Automated Coronary Tree Labeling Using Bidirectional Tree structured Recurrent Neural Networks", Vol. 99, published 27 Jun. 2019. In general, labelling algorithms are of a generic nature and applicable to other labelling schemes as well.

As a result of these three processing steps for segmenting and labelling, it is known for each point in the coronary arteries to which coronary artery segment it belongs, the shape of the coronary artery lumen, the course of the segments and, if the mentioned class of centerline tracing algorithms is used, also the course of coronary artery bypass grafts, if applicable.

Preferably, when determining second evaluation data relating to atherosclerotic disease, the at least one second evaluation algorithm, in particular based on the centerlines, detects and analyzes lesion in the coronary artery tree such that a second evaluation data set is generated for each lesion, comprising at least one information chosen from the group comprising
 a start position and end position of the lesion, in particular along the centerline,
 a plaque class, in particular chosen from calcified plaque, non-calcified plaque and mixed plaque,
 a plaque vulnerability information derived from or describing the presence of at least one vulnerability indicator, in particular chosen from low attenuation values, in particular attenuation values lower than 30 HU, positive remodeling, spotty calcification, and napkin ring signs,
 a stenting information describing the presence of a stent from an earlier intervention.

Preferably based on the coronary centerlines, the coronary lumen and the CCTA image data set, a lesion detection algorithm may detect any diseased part of the coronary arteries as at least one of the least one second evaluation algorithm. A lesion (as medical feature) may represent the full spectrum of disease, starting from very small focal lesions to rather long lesions capturing diffuse disease. During the lesion detection process, preferably, the following information may be automatically determined for each lesion:
 The start and stop positions representing positions on the coronary centerlines at the last and first healthy positions before and after the lesion. The entire path along the coronary centerlines between these positions is considered as diseased.
 Plaque composition: the lesion detection algorithm may classify the plaque composition of the lesion into calcified, non-calcified and mixed plaque.
 Plaque vulnerability: the lesion detection algorithm may identify the presence of one of the following features, which may indicate a potential vulnerability of the lesion: low attenuation values, positive remodeling, spotty calcification, and napkin ring signs. A lesion may be attributed with multiple of these vulnerability indicators at the same time. For example, positive remodeling is an outward compensatory remodeling in which the arterial wall grows outward in an attempt to maintain a constant lumen diameter, while negative remodeling is defined as a local shrinkage of vessel size. The presence of a ring of high attenuation around certain coronary artery plaques is usually called napkin ring sign. The lesion detection algorithm may further classify stents from prior interventions as such.

Example embodiments are not limited to a specific type of lesion detection algorithm. Lesion detection algorithms known from the state of the art, in particular able to determine the above-mentioned information, may be used. As an example, it is referred to U.S. Pat. No. 9,881,372 B2. If all the information described above are determined, as a result of the at least one lesion detection algorithm, it is known for each point in the coronary arteries if it is part of a coronary lesion (or a stent, if applicable). For each lesion, the plaque composition and the presence of vulnerable plaque indicators is known.

In preferred embodiments, diameter values of the coronary arteries for each lesion along the centerline are determined, in particular by at least one second evaluation algorithm and/or at least one inference rule combining at least one first evaluation data set and at least one second evaluation data set. In particular if the coronary lumen has been segmented, diameter information may be computed for each position along the coronary centerline of a lesion. Hence, the diameters at the start and stop positions of the lesion as well as the position of minimal luminal narrowing may be determined. This diameter information is also added to the evaluation database.

In an especially advantageous embodiment, the inference rules may derive result evaluation data from the first and/or second evaluation data sets for three hierarchy levels, namely a lesion level (medical feature level) relating to single lesions, a segment level relating to single segments of coronary arteries, and a patient level relating to the whole coronary artery tree. As already discussed for the general case, such a hierarchical structure further improves understandability for the user. In a concrete embodiment, regarding lesions detected by the at least one second evaluation algorithm, by the inference rules,
 on the lesion level, result evaluation data chosen from the group comprising a segment the lesion belongs to, a quantitative stenosis grade, a classification of the plaque as vulnerable or non-vulnerable and a classification as an ostium lesion or a bifurcation lesion,
 on the segment level, result evaluation data chosen from the group comprising a maximum degree of obstruction, a number of lesions and/or a lesion plaque composition, and
 on the patient level, result evaluation data, in particular the evaluation information, chosen from the group comprising a classification of the atherosclerotic disease as a one-, two-, or three-vessel disease with or without involvement of the left main segment, at least one classification grade, in particular a CAD-RADS grade, and at least one image-based score,
 may be determined.

Image-based scores may, for example, comprise a segment involvement score, a segment stenosis score, a Duke index, and/or a CT Leaman score.

Preferably, at least a part of the inference rules may follow the definitions of the SCCT Guideline and/or the CAD-RADS Reporting Guideline. For the first guideline, please see the already-referenced article by J. Leipsic et al., for the second guideline, please refer to the article by R. C. Curry et al., "Coronary Artery Disease—Reporting and Data System (CAD-RADS): An Expert Consensus Document of SCCT, ACR and NASCI: Endorsed by the ACC.", in JACC Cardiovasc Imaging 9 (2016), pages 1099-1113.

In preferred embodiments, the inference rules classify the evaluation data sets in three hierarchy levels of abstraction. On a lesion level, for each lesion, the following information may be determined. First of all, the lesion location may define the at least one coronary artery segment that is affected by the lesion. Furthermore, the quantitative stenosis grade, for example "narrowing of 53%" may be computed. This may be done, for example, by applying a traditional qualitative comparative analysis (QCA) approach, using the diameter information mentioned above derived at the start/stop position of the lesion as well as the minimum diameter within the lesion. Other interpolation schemes for estimating the healthy reference diameter are conceivable. In another approach, image-based classification may be applied, for example based on deep learning algorithms. The quantitative stenosis grade may be used to classify the lesion's severity, for example into "none", "minimal", "mild", "moderate", "severe", and "total occlusion". Furthermore, the above-mentioned plaque class (plaque composition information) and the above-mentioned plaque vulnerability information indicating presence of vulnerability indicators may be used to classify the plaque as "vulnerable" or "non-vulnerable". Finally, the position of the lesion in the coronary artery tree may be used to classify it as "bifurcation lesion" or "ostial lesion", if applicable.

Regarding the segment level, the inference rules propagate the information available on lesion level to the coronary segments. For each segment, for example, its maximum degree of obstruction, the number of lesions as well as their plaque composition may be provided.

Regarding the patient level, the classifications of the individual segments on the segment level may be used to compute different assessments of the overall state of disease in the coronary artery tree. In particular, the disease may be classified as one-/two-/three-vessel disease with or without involvement of the left main segment. Additionally or alternatively, a classification following the CAD-RADs reporting standard may be provided for the given case. For example, a grade "CAD-RADs 3/v/s" describes a maximum degree of obstruction of 50 to 69% with vulnerable plaques and presence of a stent. "CAD-RADs 0" means that no disease has been detected. Additionally, image-based scores, for example segment involvement score, segment stenosis score, Duke index and CT Leaman score may be computed and displayed.

All inferred information as well as their dependencies are, as described, added to the evaluation database as result evaluation data set or sets, such that at any time the evaluation database can be updated consistently, if required.

It is noted that the degree of luminal narrowing is just one of the relevant aspects for the assessment of the risk of future cardiovascular events. Studies have shown that the type and amount of plaques in the vessels wall help to further discriminate the risk. Especially the so-called low-attenuation plaques seem to be highly correlated with major adverse cardiac vents (MACV). Hence, plaque quantification methods may be included regarding the at least one second evaluation algorithm and/or the inference rules. In this manner, a comprehensive assessment of coronary artery disease may be provided.

In concrete embodiments, the interactive presentation may comprise, in particular as visualization data, a coronary unfolded view, in particular as overview image, and/or a schematic view, in particular as overview image, and/or at least one lesion specific view, in particular based on a curved planar reformation (CPR).

In particular, overview images may be generated for lesion level, segment level and patient level, each documenting the evaluation results. For example, the following images may be provided.

All detected coronary artery may be visualized in a single overview image together with the detected lesions and their grade as a coronary unfolded view. Graphical information may be displayed to show which parts of the coronary arteries have been detected as diseased. As an example for such an overview image, it is referred to not yet laid open European Patent application EP 19 212 538.3.

Additionally or alternatively, at least one schematic image representing a generic model of the coronary artery tree may be generated, in which the degree of obstruction of the coronary artery segment may be displayed as a color-coded image.

Furthermore, lesion-specific views may be generated as detailed images for each detected coronary lesion. Such a lesion-specific view may, for example, show a curved planar reformation of the effected vessel together with the lumen segmentation created on that coronary artery. In addition, cross-sectional views may be displayed for the lesion start and/or stop position as well as the detected position having maximal obstruction. Based on the contours the user can assess visually if the derived stenosis grading information is plausible/reasonable.

In concrete embodiments, the interactive presentation, in particular the overview and/or detailed images and/or information, may be displayed in a user interface, for example using a web-based application where the user can manually adjust and/or modify evaluation results in case he is not satisfied with first and/or second evaluation data and/or result evaluation data. On the lesion level, for example, he may modify the stenosis grade from "moderate" to "severe". As a result, a forward propagation of the modification through the evaluation database results. On lesion level, information on lesion level may be marked as not reliable/invalid. However, in embodiments, it is also possible to modify information from which a modified result evaluation data set is derived. In the mentioned example, the stenosis percentage may be updated to 70%, as this is the lower threshold value for a lesion to be classified as severe. The segment level and patient level classifications are updated accordingly. For example, a CAD-RADs grade may change from 3 to 4a. Similarly, a backtracking is performed to identify which information contributed to the modified information in the modified evaluation data set. In the given example, the stenosis grade is derived from the lumen segmentation. The modification of the user implies that the lumen segmentation was not optimal. Hence, it is hidden from the lesion-specific view. In this manner, no wrong information is displayed at any time. The display interactive presentation is always kept consistent automatically by keeping the evaluation database consistent.

Regarding automatic calcium scoring, when receiving, for example, a new DICOM study, it may be automatically verified if the examination contains at least one cardiac-gated non-contrast calcium scoring reconstruction. If not, further processing may be stopped. In the case that multiple image data sets are available, they may be prioritized based on reconstruction kernel and/or date/time information. Finally, the best suitable at least one image data set is forwarded to the subsequent processing steps.

Regarding automatic anatomy detection and labelling, the same way of proceeding as regarding the atherosclerotic disease evaluation may be used. In some embodiments, however, other segmentation schemes may be employed. Regarding the second evaluation algorithms, at least one automatic calcium scoring algorithm may be applied to the respective calcium scoring image data set. Such an automatic calcium scoring algorithm may automatically recognize single coronary calcifications and may label them according to the segment in which the calcification has been detected. Regarding an example of such an automatic calcium scoring algorithm, it is referred to the article by M. Sandstedt et al., "Evaluation of an AI-based, automatic coronary artery calcium scoring software", in Eur Radiol 30(2020), pages 1671-1678.

Each detected single coronary calcification together with its meta data, in particular comprising segment labels, may be added to the evaluation database as second evaluation data sets. As regarding the CCTA evaluation, the inference rules for calcium scoring may also derive result evaluation data for the three hierarchy levels named below, that is the lesion level relating to single lesions, the segment level relating to single segments of coronary arteries, and the patient level relating to the whole coronary artery tree. Regarding the calcium scoring, the lesion level may also be called calcification level. In a concrete embodiment, by the inference rules,

- on the calcification level, result evaluation data comprising a segment the calcification belongs to,
- on the segment level, result evaluation data chosen from the group comprising a calcification score, a number of calcifications and/or a volume of the calcifications, and
- on the patient level, result evaluation data, in particular the evaluation information, chosen from the group comprising a respectively the calcification score, a number of calcifications, a volume of the calcifications, a percentile of the patient, and an arterial age of the patient, may be determined. For example, the definitions in the already mentioned article by C. H. McCollough et al. may be followed.

Regarding calcification scores, the total and segment-specific Agatston score may be determined. Furthermore, the total and segment-specific volume of the calcifications may be provided. The total number of calcifications may be provided on the segment level as well as on the patient level. Furthermore, a patient percentile may be computed to choosing a reference population, for example based on patient information like gender, age and the like. For reference populations, for example, the MESA database may be used (see A. L. McClelland et al., "Distribution of coronary artery calcium by race, gender, and age: results from the Multi-Ethnic Study of Atherosclerosis (MESA)", Circulation 113(2006), Seiten 30-37.

Finally, based on a patient's gender, age, ethnicity and/or other patient information and a reference population, the arterial age may be computed. An arterial age computation was, for example, published in an article by R. L. McClelland et al., "Arterial Age as a Function of Coronary Artery Calcium (from the Multi-Ethnic Study of Atherosclerosis [MESA])", Am J Cardiol. 2009 Jan. 1; 103(1), pages 59-63.

Also in this case, all inferred evaluation results are, of course, added to the evaluation database including their dependencies/linkage by inference rules.

Regarding the interactive presentation of the evaluation results, for calcium scoring, overview images may again be generated for lesion level (calcification level), segment level and patient level, which document the segmentation and calcification results. In a concrete embodiment, a calcium overview image may be provided which visualizes all detected calcifications in maximum intensity projections through the imaging region in a color-coded way. In this manner, from a single image, it can be seen which calcifications have been detected and if there are potentially missed lesions. The calcium overview image also allows to get a high-level understanding if the calcifications are attributed to the correct vessel/segment. Additionally or alternatively, the original computed tomography slices may be provided with the labelled calcifications as overlay to enable a detailed evaluation of the calcification labelling at, for example, the left main bifurcation. Finally, a percentile chart relating to at least one calcium score may be included in the interactive presentation. Such a percentile chart may visualize the patient-specific calcification score, for example Agatston score, in the context of the selected reference population. Regarding calcium scoring, it is noted that only few modifying operations need to be supported in the interactive presentation. For example, the user may manually change the patient information and/or a selected reference database. Any manual change of these values triggers an update of the risk categorization, in particular the percentile information and/or the arterial age.

In further embodiments, the at least one image data set may comprise functional image data of the coronary artery tree, wherein, as evaluation data, at least one hemodynamic parameter, in particular a fractional flow reserve (FFR), is determined. Hence, example embodiments may also provide functional assessment of coronary artery disease. In particular regarding lesions of intermediate severity, a functional assessment is recommended by guidelines. While hemodynamic measurements have traditionally been performed by actually measuring inside the blood vessels, in particular measuring the pressure drop across a lesion (fractional flow reserve—FFR), it has recently been proposed to also determine hemodynamic parameters non-invasively based on imaging techniques. For example, FFR values may be determined from computed tomography image data sets based on simulation and/or machine learning. Additionally or alternatively, other approaches for hemodynamic assessment, like coronary volume-to-mass-ratio and/or lesion-subtended myocardial mass can also be employed.

In an extension, in addition to evaluating the calcification in the coronary artery tree, evaluation data regarding calcification in the heart valves and/or the aortic root may be determined by at least one second evaluation algorithm and/or inference rule. In this manner, calcifications in the aortic root and/or heart valves can also be quantified. According to guidelines, a CCTA and/or CaSc report should also include a statement regarding the presence of calcifications in the aortic root and the heart valves. If present, the amount of calcification should be graded into mild/moderate/severe. Hence, advantageously, the method and systems of example embodiments can be extended to also provide support for detection and/or grading of calcifications in the aortic root and heart valves.

Furthermore, in preferred embodiments, at least one heart parameter may be determined as additional evaluation data by at least one second evaluation algorithm and/or inference rule, in particular at least one heart chamber volume and/or at least one heart muscle size. For example, based on contrasted and/or non-contrasted cardiac computed tomography image data sets, segmentation of the ventricles and the atrium is also possible. Based on such segmentation results, a quantification of the individual chamber size as well as the sizing of the heart muscle is possible. If image data sets have been acquired at more than one point in time, additionally, the left and right ventricular function may be quantified. Quantification algorithms regarding heart parameters have already been proposed in the state of the art and may also be applied in example embodiments.

Of course, the general concept of providing an explainable artificial intelligence evaluation system aggregating localized anatomical and/or pathological findings and measurements via inference rules to more abstract region- or patient-wise assessments, as described by example embodiments, can also be applied to other radiological examinations. For example, a method according to at least one example embodiment may be used for evaluating image data sets of a liver examination and/or a digital breast tomosynthesis examination.

An evaluation system according at least one example embodiment for evaluating at least one image data set of an imaging region of a patient to determine at least one evaluation information describing at least one medical condition in an anatomical structure of the imaging region comprises:
   an image interface for receiving the at least one image data set,
   a storage for storing an evaluation database and a rule set,
   at least one first determination unit for segmenting and labelling the anatomical structure using at least one first evaluation algorithm to generate at least one first evaluation data set and determining at least one second evaluation data set describing at least one local medical feature in the anatomical structure using at least one second evaluation algorithm, wherein the at least one first determination unit is adapted to enter the at least one first and the at least one second evaluation data set into the evaluation database,
   a second determination unit for determining the at least one evaluation information by applying inference rules of the rule set, wherein each inference rule derives at least one result evaluation data set from at least one, in particular at least two, input evaluation data set, wherein the second determination unit is adapted to augment the evaluation database by adding the result evaluation data sets for each rule application linked to the respective input evaluation data sets in the evaluation database,
   a user interface unit for outputting an interactive presentation comprising information from at least a part of the evaluation data sets of the evaluation database, wherein the initially displayed interactive presentation comprises at least one of the at least one evaluation information and the user interface is adapted to receive a user interaction command related to at least one chosen result evaluation data set and to update the interactive presentation to include information of at least one input evaluation data set from which the chosen result evaluation data set is derived.

All features and remarks relating to the evaluation method of example embodiments accordingly apply to the evaluation system according to example embodiments, such that the same advantages can be accomplished. In particular, the evaluation system may be configured to perform a method according to example embodiments. The evaluation system may comprise at least one computing device, in particular comprising the at least one storage and/or at least one processor. The functional units may, in particular, be implemented at least partially in hardware and/or at least partially in software. Further functional units regarding embodiments of the method may, of course, be added. Preferably, the evaluation system may also comprise an output interface, in particular for outputting the combination data set, in particular the whole evaluation database, for example to a picture archiving and communication system (PACS) and/or an information system and/or an electronic health record. In particular, such an output interface may also serve as an input interface, in particular the image interface, if image data sets and/or input data comprising the image data sets, for example a DICOM study, are retrieved from the PACS and/or the information system and/or the electronic health record. As already explained, the evaluation system may be a stand-alone system, but may also be integrated into other systems and devices, for example in an imaging device or, preferably, in a reading work station.

A computer program according to at least one example embodiment can be directly loaded into a storage device of a computing device of an evaluation system and comprise program such that, if the computer program is executed on the computing device of the evaluation system, the steps of a method according to the at least one example embodiment are performed. The computer program may be stored on an electronically readable storage medium according to at least one example embodiment, which thus comprises control information comprising at least one computer program according to the at least one example embodiment, such that, if the electronically readable storage medium is used in a computing device of an evaluation system, a method according to the at least one example embodiment is performed. The electronically readable storage medium according to at least one example embodiment may preferably be a non-transitory storage medium, for example a CD-ROM.

FIG. 1 is a flow chart showing high-level steps of a method according to at least one example embodiment. In a step S1, which is an optional preparatory step, input data comprising at least one image data set is received. For example, input data may be provided as a DICOM file of a certain examination (often also called a DICOM study). The input data is automatically passed and categorized according to the evaluation purpose. If no image data sets regarding the evaluation purposes provided by the concrete embodiment are found, processing is stopped. If multiple image data sets relating to a served evaluation purpose are available in the input data, they may be prioritized according to specific prioritization rules. In particular, for each evaluation purpose served, the ensuing automated processing is triggered using the at least one best suitable image data set (for example highest priority). In the preparatory step S1, furthermore, image data sets can be pre-processed, for example regarding the distribution of image data, performance and the like. For example, in a motion-triggered acquisition, image data sets may be generated for different motion phases, and the best suitable image data set may be chosen.

In a step S2, automatic anatomy detection and labelling takes place using at least one first evaluation algorithm. The at least one first evaluation algorithm preferably comprises at least one deep learning-enabled automatic segmentation algorithm to extract the relevant parts of anatomy, in particular the anatomical structure of interest for the evaluation purpose. Geometrical models may be generated and automatically labelled using a labelling scheme. For example, the anatomical structure may be divided into segments each being named using a proper medical terminology. The labelling scheme may follow a defined hierarchical structure comprising at least two hierarchy levels, in the simplest case the whole anatomical structure as the highest hierarchy level and segments as the lowest hierarchy level. However, more than two hierarchy levels are conceivable, for example regarding a blood vessel tree, where the blood vessel tree can be divided into different blood vessels (first segments), which again may be divided into blood vessel segments (second, lower-level segments). It is noted that the local medical features detected in step S3 provide a further, additional low hierarchy level in this context. As a result of step S2, each point in the anatomical structure can be associated with a segment, whose designation is known.

In step S3, medical features are automatically detected and associated meta data is determined using at least one second evaluation algorithm. Preferably, the at least one second evaluation algorithm comprises at least one deep learning-enabled detection algorithm. That is, preferably, both the at least one first evaluation algorithm and the at least one second evaluation algorithm, which use at least one of the at least one image data set as input data, comprise at least one trained evaluation function. The automatic detection process provides the location of the medical feature, for example a lesion and/or pathology, as well as meta data associated with the medical feature, for example a characterization of the medical feature or information relating to disease severity. The availability of specific meta data attributes depends on the actual models used during the detection procedure.

The results of the steps S2 and S3 are first evaluation data and second evaluation data, respectively, as first and second evaluation data sets. These first and second evaluation data sets are entered into an evaluation database.

In a step S4, the rule-based diagnostic workup using a rule set comprising at least one inference rule is performed, such that the evaluation database, in which all knowledge regarding the current case is gathered, can be augmented by further, result evaluation data sets. The evaluation database is processed by the inference rules, which may comprise logical operations, statistical operations and/or if-then-else-rules and other linking operations. In particular, further patient data and/or statistical data can also be evaluated by at least a part of the inference rules, for example patient gender, patient height, patent size, patient age, patient ethnicity and the like. Statistical data may preferably relate to reference populations to determine evaluation data, in particular evaluation information, like percentiles and/or anatomical age. While the rules may, in particular, at least partially concern physical and/or technical correlations, they may at least partially also encode knowledge from societal guidelines, for example definitions of certain disease scores and/or other clinically relevant evaluations results. Each inference rule uses at least one input evaluation data set from the evaluation database and results in at least one result evaluation data set. The derived knowledge of the result evaluation data set is added back to the evaluation database. Of course, also the inference rules linking the evaluation data sets are stored in the evaluation database, such that the information in the database can be kept consistent at any time. It is noted that this rule-based diagnostic workup may also join information derived from multiple image data sets and even multiple evaluation purposes, in particular, as already described, with other information sources, like, for example, from external information systems.

It should be noted at this point that the (minimal), designated evaluation purpose is the determination of at least one evaluation information. This evaluation information, which may be a disease score, a total quantification of a certain substance or the like, is comprised by the evaluation data of the evaluation database, in particular as some final result evaluation data in at least one result evaluation data set, for example at the highest hierarchy level. However, the method described here derives and stores additional evaluation data to create a sort of expert system being able to explain how the evaluation information was derived and, in particular present underlying information or even image data. In other words, by using the evaluation database and all evaluation data contained in it, the user can understand how the method came to its conclusions based on the provided image data and, in particular also allows the user to influence the automatically prepared evaluation results, in particular the evaluation information, in an efficient way, as will be further described below.

In a step S5, an interactive presentation is generated and provided at a user interface. The interactive presentation serves to present the evaluation results. The interactive presentation may comprise image data from the at least one image data set, visualization data derived from at least one of the at least one image data set and/or from at least one evaluation data set, and/or especially generated overview images. For example, image data or visualization data may be annotated, overlayed and/or modified, for example color-coded, to include information from the evaluation database in the corresponding images. Preferably, the interactive presentation may be oriented at the hierarchy levels discussed above, for example summarizing information on the medical feature level, at least one low hierarchy level, for example a segment level, and at least one high hierarchy level, for example anatomical structure level or patient level. As the evaluation information, in many cases, relates to the highest hierarchy level, for example the patient level, an initially displayed interactive presentation may mainly focus on this highest hierarchy level and also show at least a part of the evaluation information. The user may then interact with the interactive presentation using user interaction commands such that the interactive presentation may be updated to include further evaluation data from the evaluation database, in particular information underlying an information item, in particular evaluation data set, the user interaction was related to.

Regarding the medical feature level, for example lesion level, detailed images may be generated for each detected medical feature, which may in particular also show information from the first and second evaluation data sets. By verifying the inferred evaluation data against further displayed information, in particular the detailed image, a user can, at any time, assess the plausibility of the evaluation result.

If the user does not agree with one or more evaluation results, he can manually modify evaluation data in the evaluation database. Hence, in a step S6, it is checked whether user input regarding a modification is received, in which case the respective at least one evaluation data set is accordingly modified and the evaluation database is updated in workup step S4, also leading to an update of the interactive presentation in step S5. As the evaluation data sets are all linked by the inference rules, by using a forward chaining mechanism, all evaluation data effected by the modification can be updated. In some cases, it may also be possible to update evaluation data from which the modified evaluation data set was derived. For example, if a classification is changed, a value underlying this classification may be moved into an interval corresponding to this classification. Alternatively or additionally, information from which the modified evaluation data set was derived may also be marked as less reliable, in particular invalid and/or outdated. All evaluation data linked to modified evaluation data may also be marked in the interactive presentation, such that the user can immediately see which information was updated due to his modification.

If, however, in step S6, the user approves the contents of the evaluation database, in particular the evaluation information, in a step S7, the evaluation results may be persisted and/or distributed to other systems, in particular in structured and/or pictorial format, for example based on the DICOM standard. In other words, a combination data set may be compiled from the evaluation database including all relevant image data and/or evaluation data. For example, a DICOM study initially received in step S1 may be supplemented with further information from the evaluation data sets and archived in a PACS and/or electronic health record. Of course, it is also possible to provide evaluation results via an output interface to a reporting system and/or a decision support system.

A concrete embodiment enabling the combined evaluation of a coronary computed tomography angiography scan and a calcium scoring scan will now be described, in particular regarding the interactive presentation. Such a cardiac study, which may be supplied as a DICOM study, as already discussed, refers to the coronary artery tree as an anatomical structure and usually, as the evaluation purpose, has the goal to determine at least one atherosclerotic disease score and at least one calcification score as evaluation information. According to known labelling schemes already discussed in the general part of the description, the coronary artery tree may be divided into a plurality of segments, such that evaluation results will be generated and presented on a medical feature level (lesion level/calcification level), a segment level and a patient level/anatomical structure level.

Regarding step S1, if a new DICOM study of the heart of a patient is received, the examination may, in preferred embodiments, be split into image data sets relating to different phases of the heart cycle. This is possible because usually, CCTA scans are cardiac-gated. From these image data sets relating to different heart phases, the best suitable can be chosen, which, in this case, may be the image data set showing the least coronary motion. Of course, also other quality parameters may be derived to determine a suitability measure, such that the image data set having the highest suitability measure can be chosen for further processing regarding the CCTA evaluation. If multiple image data sets suitable for calcium scoring evaluation are received, also, quality parameters relating to requirements for evaluation may be determined and the best suitable image data set may be selected. For example, quality parameters in the case of the calcium scoring evaluation may be related to the used reconstruction kernel.

Regarding step S2, for the CCTA evaluation, three substeps may be used, namely detection of the coronary artery centerlines by a centerline tracing algorithm, detection of the coronary artery lumen by a lumen segmentation algorithm and classifying and labelling the detected coronary arteries according to a labelling scheme using a labelling algorithm. As a result of these three substeps, from the resulting first evaluation data set, it is known for each point in the coronary arteries to which coronary segment they belong, which the shape of the coronary artery lumen is and how the local course of the segments is. If coronary artery bypass grafts are also detected by one of these first evaluation algorithms, their course also becomes known, if applicable.

Regarding automatic calcium scoring, these results may also be used.

In step S3, for the CCTA evaluation, at least one lesion detection algorithm is used as the at least one second evaluation algorithm. Preferably, the resulting second evaluation data set for each lesion comprise the lesion start and stop position along the centerlines, the plaque composition (calcified, non-calcified, or mixed), a plaque vulnerability information describing the presence of plaque vulnerability indicators like low attenuation, positive remodeling, spotty calcification and/or napkin ring signs, and whether the lesion is classified as a stent from a prior intervention.

Regarding the calcium scoring evaluation, single calcifications are detected, located, and quantified and the respective second evaluation data sets are stored in the evaluation database.

In step S4, regarding the CCTA evaluation, diameter information may be derived from the lumen information in the at least one first evaluation data set for each lesion. Further inference rules may follow the definitions of the SCCT guideline and/or the CAD-RADS reporting guideline already cited above. For example, a rule may comprise checking whether an obstruction percentage is in a certain interval and/or whether the lumen diameter exceeds a certain threshold. Other rules may additively and/or multiplicatively combine evaluation data values, or, generally, comprise calculation formulas.

In this preferred embodiment, the inference rules classify the detected information in three hierarchy levels of abstraction, namely the lesion level, the segment level and the patient level. Regarding the lesion level, the following evaluation data is provided: lesion location (which at least one coronary artery segment the lesion affects), quantitative stenosis grade, a classification of the plaque as vulnerable or non-vulnerable, and a classification as ostium lesion or bifurcation lesion, if applicable. On the segment level, a maximum degree of obstruction, a number of lesions and/or a lesion plaque composition may be comprised by result evaluation data. Finally, on the patient level, result evaluation data derived by the inference rules may comprise a classification of the atherosclerotic disease as a one-, two-, or three-vessel disease with or without involvement of the left main segment, at least one classification grade, and at least one image-based score. These derived evaluation data may all be evaluation information requested as evaluation purpose. For example, a classification following the CAD-RADs reporting standard may be provided, together with image-based scores like segment involvement score, segment stenosis score, duke index, and CT Leaman score.

Regarding the automatic calcium scoring evaluation, the Agatston score may be provided on patient level and segment level, as well as a volume score describing the total and segment-specific volume of the calcifications. Further, on segment level and patient level, the total number of calcifications may be provided. Finally, on patient level, a percentile regarding a reference population and/or an arterial age may be determined and provided.

Figure 2:
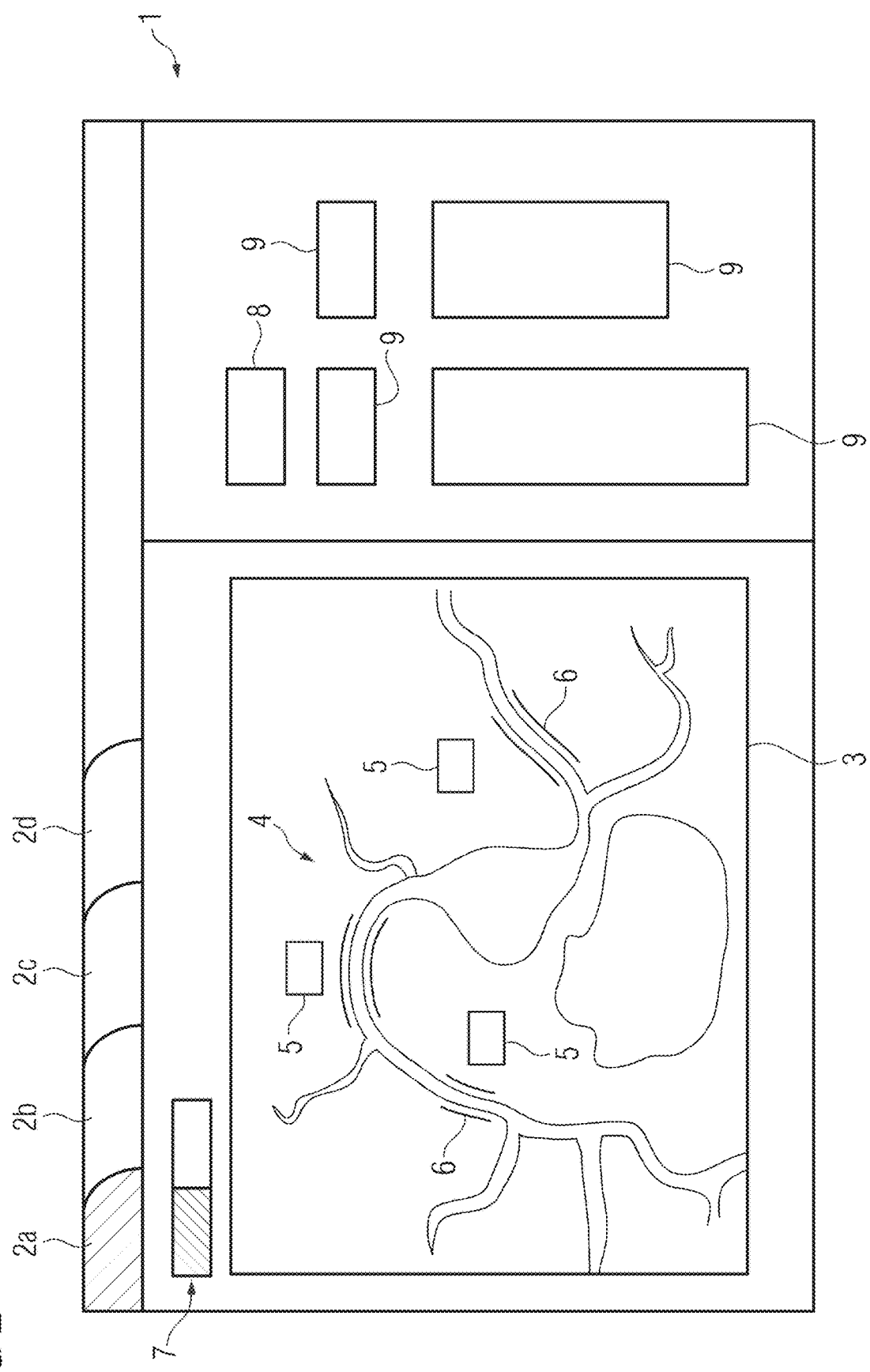

FIGS. 2 to 5 illustrate the interactive presentation of results in an embodiment, wherein the results of the CCTA evaluation and the calcium scoring evaluation are presented in one and the same user interface 1. FIG. 2 shows an initial view provided after evaluation in steps S1 to S4 is completed. A first tab 2a of the user interface 1 is active, such that an overview over the CCTA evaluation results is displayed. The further tabs 2b, 2c and 2d relate to segment level information regarding CCTA, lesion level information regarding the CCTA, and calcium scoring evaluation information, respectively.

On the left side in FIG. 2, an overview image 3, in this case a coronary unfolded view generated from the at least one CCTA image data set, is displayed, showing the anatomical structure 4, in this case the coronary artery tree, with annotations 5 and overlays 6 relating to at least a part of the detected lesions. As can be seen, lesions are marked by partially enframing the respective coronary artery sections, for example in yellow, while textual information can be added as annotations 5. Using buttons 7, another overview image, in particular a schematical overview image, can be alternatively selected.

On the right side of user interface 1, information from the evaluation data relating to the patient level is shown, in particular the evaluation information 8 and further evaluation data 9. The patient level evaluation results shown here may comprise the CAD-RADs grade, the disease type and/or risks scores. At least for a part of the displayed information from the evaluation database, the user may interact to modify evaluation data and/or receive additional information, in particular in a view as further discussed below.

Figure 3:
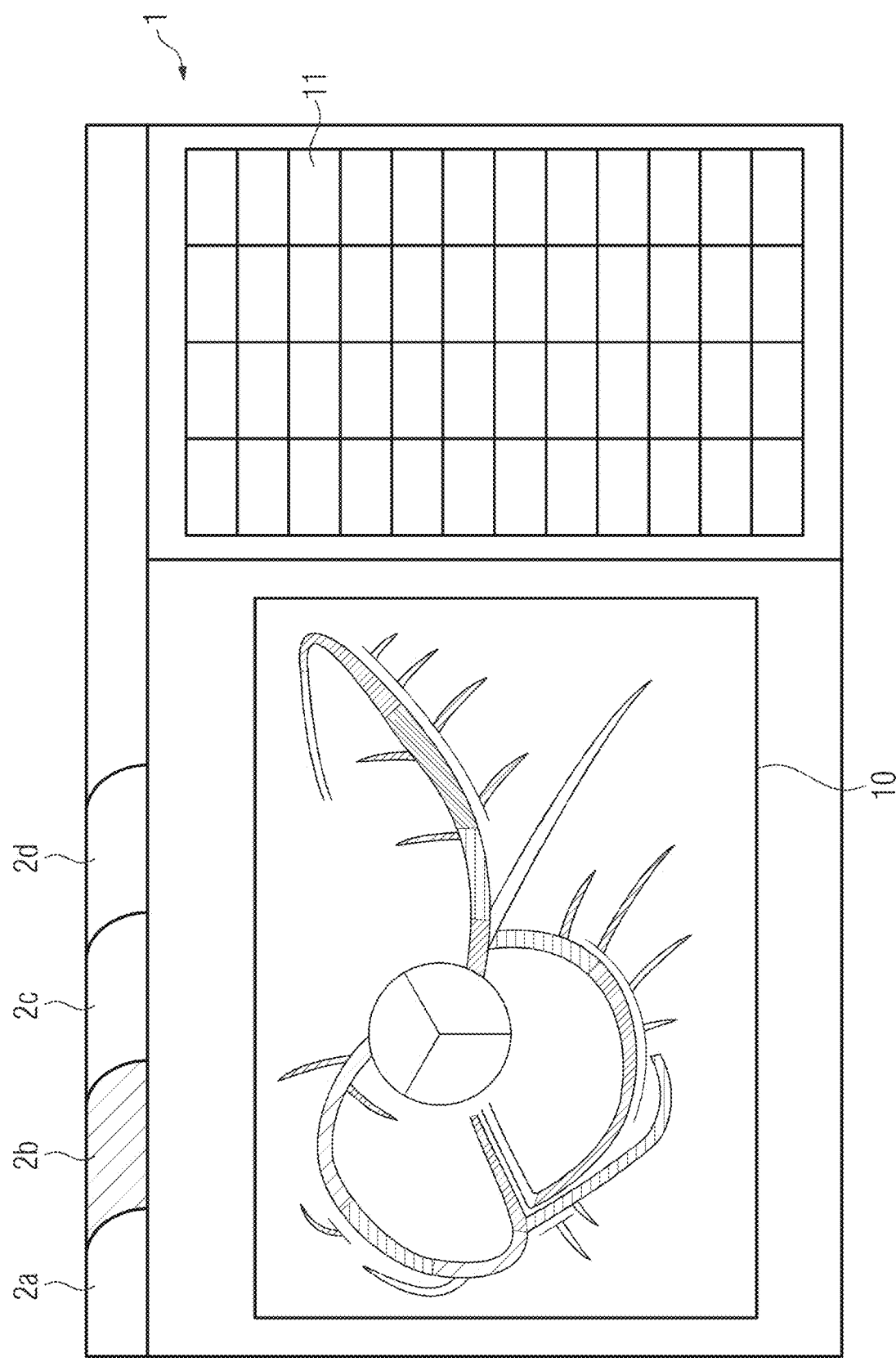

FIG. 3 shows the segment level tab 2b, in this case comprising a schematic overview image 10, in which the segments of the coronary artery tree are color-coded according to the severity of their lesions. The segment level evaluation results are further displayed as text in a table 11 on the right side of the user interface 1.

Figure 4:
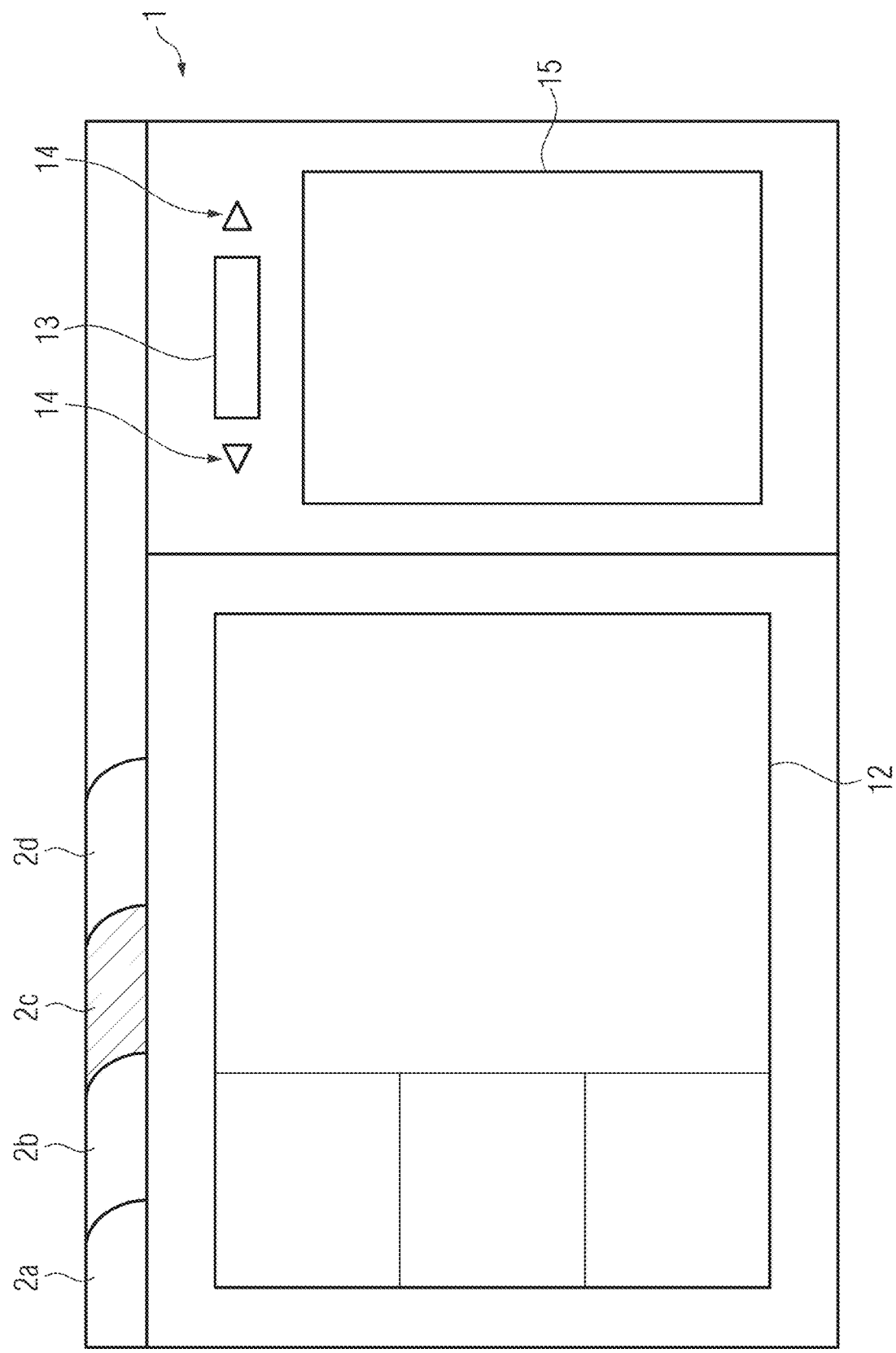

FIG. 4 shows the user interface of the interactive presentation when the CCTA lesion level tab 2c is active. On the left side, a detailed image 12 which may be composed of several sub-images regarding a certain lesion is shown. This lesion is indicated by text 13, while the lesions can be passed using buttons 14. Of course, if a user interaction command regarding one of the lesions for segments shown in the previous states of the interactive presentation is received, the corresponding lesion is directly selected and shown. In the detailed image 12, the start position, the stop position and the position of maximum narrowing may be documented together with the lumen segmentation. First and second evaluation data as well as result evaluation data relating to the lesion are displayed in area 15.

Figure 5:
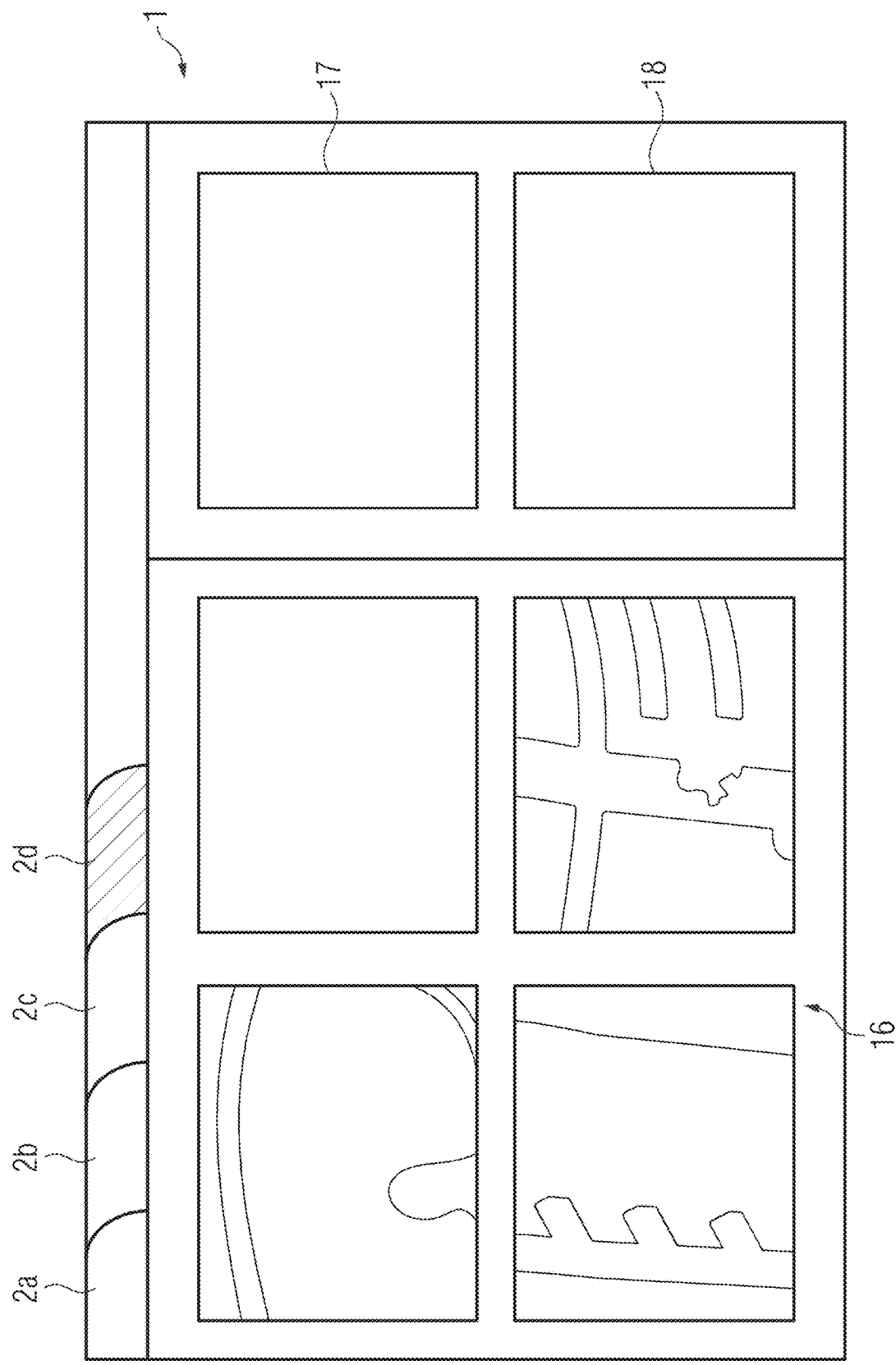

Finally, FIG. 5 shows the user interface 1 when the calcium scoring tab 2d is active. In this case, on the left side, an overview image 16 visualizes the detected calcifications according to the segment they have been attributed to. On the right side evaluation data 17, 18 regarding the segment level and the patient level, respectively, is displayed. The information from the patient level, evaluation data 17, also comprises the evaluation information regarding calcium scoring.

Figure 6:
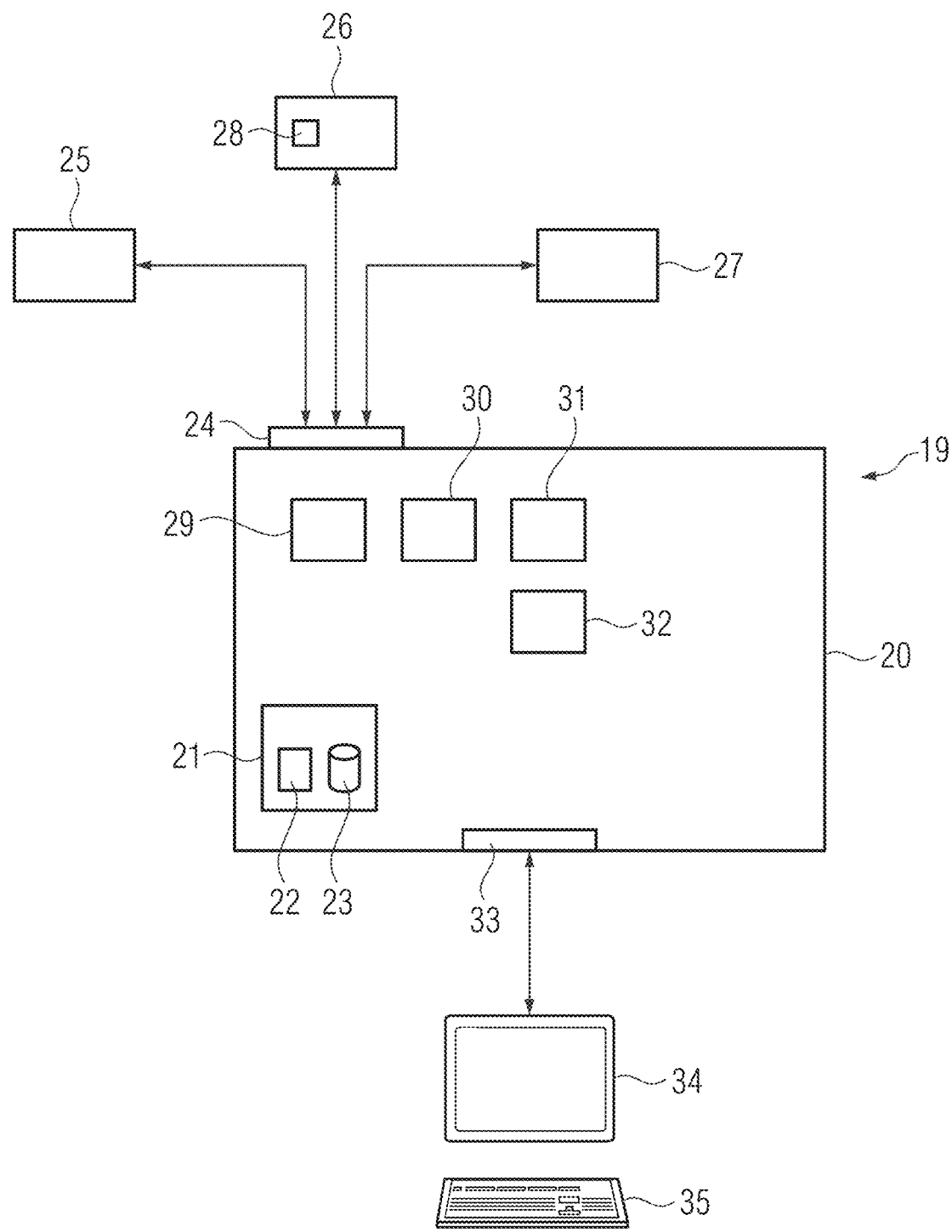

FIG. 6 is a schematic drawing of an evaluation system 19 according to at least one example embodiment. The evaluation system 19 comprises at least one computing device 20 having a storage device 21 and at least one processor. In the storage device 21, the rule set 22 and the evaluation database 23 may be stored.

The evaluation system 29 comprises a first input and output interface 24, by which the evaluation system 19 is connected to at least one imaging device 25, at least one information system 26 and at least one PACS 27. Image data sets, in particular in a DICOM study, may be received via the interface 24 from the imaging device 25, the information system 26 and/or the PACS 27. In the information system 26, for example, electronic health records 28 of patients may be stored. Furthermore, the at least one information system 26 may provide statistical data regarding reference populations.

If a DICOM study is received via the interface 24, it is prepared for evaluation in an optional preparation unit 29 implementing step S1. A first determination unit 30 applies the first and second evaluation algorithms according to steps S2 and S3 of FIG. 1, and stores the resulting first and second evaluation data sets into a study-specific or even evaluation purpose-specific evaluation database 23. In a second determination unit 31, the inference rules of the rule set 22 are applied according to step S4, augmenting the evaluation database 23. It is noted that additional information can be taken into account by the second determination unit 31, for example from patient data and/or statistical data also received via the interface 24, for example from the information system 26. In a user interface unit 32, the interactive presentation is generated and managed, in particular also regarding user input and user interaction commands. Via a second input/output interface 33, a display device 34 and an input device 35 may be controlled and user input as well as user commands may be received. If a user-initiated modification of at least one evaluation data set in the evaluation database 23 is performed, the second determination unit 31 again applies the inference rules of the rule set 22 to update all evaluation data sets effected by the modification.

If a user approval input is received in the user interface unit 32, the combination data set may be compiled according to step S7 and distributed via interface 24 for storing or further processing/viewing.

In a preferred embodiment, the evaluation system 19 may be integrated into a reading work station, which then also comprises the display device 34 and the input device 35. In other embodiments, the evaluation system 19 may be provided as a stand-alone system, integrated into an imaging device 25, or coupled to a reporting system and/or decision support system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Further, as noted similarly above, the use of the undefined article "a" or "one" does not exclude that the referred features can also be present several times. Likewise, the term "unit" or "device" does not exclude that it includes several components, which may also be spatially distributed.

Although at least some example embodiments have been described in detail, example embodiments are not limited by the disclosed examples from which the skilled person is able to derive other variations without departing from the scope of example embodiments.

The invention claimed is:

1. A computer implemented method for evaluating at least one image data set of an imaging region of a patient, wherein at least one evaluation information describing at least one medical condition in an anatomical structure of the imaging region is determined, the method comprising:

preprocessing the at least one image data set, the at least one image data set including at least one cardiac-gated coronary computed tomography angiography scan and at least one calcium scoring computed tomography scan;

segmenting and labelling the anatomical structure using at least one first evaluation algorithm to generate at least one first evaluation data set and entering the at least one first evaluation data set into an evaluation database, the anatomical structure being a coronary artery tree and the segmenting and labelling including detecting, by at least one of the at least one first evaluation algorithm, centerlines of coronary arteries of the coronary artery tree, detecting, by at least one of the at least one first evaluation algorithm, a coronary lumen surrounding the centerlines of the coronary arteries, and classifying the coronary arteries of the coronary artery tree into segments for labelling by at least one of the at least one first evaluation algorithm according to at least one of a defined classification scheme or a user-selectable classification scheme of the coronary artery tree, such that the at least one first evaluation data set describes, for each point in the coronary artery tree, a segment to which the point belongs, a local course of the segment, and a local shape of the segment;

determining at least one second evaluation data set describing at least one local medical feature in the anatomical structure using at least one second evaluation algorithm and entering the at least one second evaluation data set into the evaluation database;

determining the at least one evaluation information by applying inference rules of a rule set, wherein each inference rule derives at least one result evaluation data set from at least one input evaluation data sets and wherein the evaluation database is augmented by adding the result evaluation data sets for each rule application linked to the respective input evaluation data sets in the evaluation database; and outputting an interactive presentation comprising information from at least a part of the evaluation data sets of the evaluation database, wherein an initially displayed interactive presentation comprises at least one of the at least one evaluation information and, when a user interaction command related to at least one chosen result evaluation data set is received, updating the interactive presentation to include information of at least one input evaluation data set from which the chosen result evaluation data set is derived, wherein during the preprocessing the cardiac-gated coronary computed tomography angiography scan is split into several image data sets according to multiple phases of a heart cycle, at least one of the image data set of a defined heart phase is selected for evaluation or at least one of the image data set or a subset of the at least one image data set best meeting requirements of at least one of the at least one first evaluation algorithm or the at least one second evaluation algorithm is forwarded to a respective at least one of the at least one first evaluation algorithm or the at least one second evaluation algorithm, and the evaluation information comprises at least one atherosclerotic disease-related score and at least one calcium score for the patient.

2. The method according to claim 1, wherein the interactive presentation at least one of (i) image data from the image data set, (ii) visualization data derived from at least one of the at least one image data set or from at least one evaluation data set, or (iii) at least one overview image.

3. The method according to claim 2, wherein at least a part of the information from the evaluation data sets included in the interactive presentation is presented by at least one of annotating presented image data, overlaying the presented image data, modifying the presented image data or the visualization data.

4. The method according to claim 1, wherein at least one evaluation data set is modified based on received user input, wherein all evaluation data sets linked to the modified evaluation data sets in the evaluation database are at least one of (i) marked, (ii) all result evaluation data sets derived using the modified evaluation data sets are updated using the respective inference rules, (iii) at least a part of at least one evaluation data set or sets from which a modified evaluation data set was derived is marked as less reliable, or (iv) excluded from the interactive presentation.

5. The method according to claim 1, wherein the anatomical structure is hierarchically divided into segments in multiple hierarchy levels, wherein at least a part of the result data sets (i) is determined for a defined hierarchy level or (ii) comprises evaluation data relating to a defined segment.

6. The method according to claim 5, wherein the rules set comprises at least one of (i) inference rules for deriving lowest hierarchy level result evaluation data sets from at least one of the at least one second evaluation data sets, respectively, or (ii) inference rules deriving a higher hierarchy level result evaluation data set from at least one lower hierarchy level input evaluation data set.

7. The method according to claim 1, wherein at least one of additional patient data or statistical data are received, wherein information from at least one of the additional patient data or the statistical data is used by at least one inference rule.

8. The method according to claim 1, wherein, if a finalizing user command is received, a combination data set comprising at least one of the at least one image data set or at least a part of the evaluation data of the evaluation data sets, is compiled and provided for storing.

9. The method according to claim 1, further comprising:
deciding, in which, before applying any first or second evaluation algorithm, the at least one image data set is analyzed regarding (i) suitability for at least one of the first evaluation algorithm or the second evaluation algorithm, (ii) to determine at least one of a suitable first evaluation algorithm or a suitable second evaluation algorithm, or (iii) if multiple image data sets are received, associate the image data sets to sets of the at least one of the first evaluation algorithm or the second evaluation algorithm.

10. The method according to claim 1, wherein, after the at least one first evaluation data set has been determined, which describes segments of the coronary artery tree, for at least one of at least one segment or at least one group of segments, the determination of meeting the requirements is performed on subsets only showing at least one of the segment or group, respectively.

11. The method according to claim 1, wherein the at least one second evaluation algorithm detects and analyzes lesions in the coronary artery tree such that a second evaluation data set is generated for each lesion, comprising at least one information chosen from a group comprising
a start position and end position of the lesion, a plaque class,
a plaque vulnerability information derived from or describing a presence of at least one vulnerability indicator, positive remodeling, spotty calcification, and napkin ring signs, or
a stenting information describing the presence of a stent from an earlier intervention.

12. The method according to claim 1, wherein the inference rules derive result evaluation data from at least one of the first evaluation data set or the second evaluation data set for three hierarchy levels, the three hierarchy levels including a lesion level relating to single lesions, a segment level relating to single segments of coronary arteries, and a patient level relating to the whole coronary artery tree.

13. The method according to claim 1, wherein the interactive presentation includes at least one of a coronary unfolded view, a schematic view, at least one lesion-specific view, or a percentile chart relating to the at least one calcium score.

14. An evaluation system for evaluating at least one image data set of an imaging region of a patient to determine at least one evaluation information describing at least one medical condition in an anatomical structure of the imaging region, the evaluation system comprising:
an image interface configured to receive and preprocess the at least one image data set, the at least one image data set including at least one cardiac-gated coronary computed tomography angiography scan and at least one calcium scoring computed tomography scan;
a storage device configured to store an evaluation database and a rule set;
at least one first determination unit configured to segment and label the anatomical structure using at least one first evaluation algorithm to generate at least one first evaluation data set and determine at least one second evaluation data set describing at least one local medical feature in the anatomical structure using at least one second evaluation algorithm, wherein the at least one first determination unit is adapted to enter the at least one first and the at least one second evaluation data set into the evaluation database, the anatomical structure being a coronary artery tree and the at least one first determination unit configured to segment and label the anatomical structure by
detecting, by at least one of the at least one first evaluation algorithm, centerlines of coronary arteries of the coronary artery tree,
detecting, by at least one of the at least one first evaluation algorithm, a coronary lumen surrounding the centerlines of the coronary arteries, and
classifying the coronary arteries of the coronary artery tree into segments for labelling by at least one of the at least one first evaluation algorithm according to at least one of a defined classification scheme or a user-selectable classification scheme of the coronary artery tree,
such that the at least one first evaluation data set describes, for each point in the coronary artery tree, a segment to which the point belongs, a local course of the segment, and a local shape of the segment;
a second determination unit configured to determine the at least one evaluation information by applying inference rules of the rule set, wherein each inference rule derives at least one result evaluation data set from at least one input evaluation data set, wherein the second determination unit is adapted to augment the evaluation database by adding the result evaluation data sets for each rule application linked to the respective input evaluation data sets in the evaluation database; and
a user interface unit configured to output an interactive presentation comprising information from at least a part of the evaluation data sets of the evaluation database, wherein an initially displayed interactive presentation comprises at least one of the at least one evaluation information and the user interface is adapted to receive a user interaction command related to at least one chosen result evaluation data set and to update the interactive presentation to include information of at least one input evaluation data set from which the chosen result evaluation data set is derived, wherein
during the preprocessing the cardiac-gated coronary computed tomography angiography scan is split into several image data sets according to multiple phases of a heart cycle,
at least one of the image data set of a defined heart phase is selected for evaluation or at least one of the image data set or a subset of the at least one image data set best meeting requirements of at least one of the at least one first evaluation algorithm or the at least one second evaluation algorithm is forwarded to a respective at least one of the at least one first evaluation algorithm or the at least one second evaluation algorithm, and
the evaluation information comprises at least one atherosclerotic disease-related score and at least one calcium score for the patient.

15. A non-transitory computer readable storage medium having instructions that, when executed by a computing device of an evaluation system, are configured to cause the evaluation system to perform a method for evaluating at least one image data set of an imaging region of a patient, wherein at least one evaluation information describing at least one medical condition in an anatomical structure of the imaging region is determined, the method comprising:
preprocessing the at least one image data set, the at least one image data set including at least one cardiac-gated coronary computed tomography angiography scan and at least one calcium scoring computed tomography scan;
segmenting and labelling the anatomical structure using at least one first evaluation algorithm to generate at least one first evaluation data set and entering the at least one first evaluation data set into an evaluation database, the anatomical structure being a coronary artery tree and the segmenting and labelling including
detecting, by at least one of the at least one first evaluation algorithm, centerlines of coronary arteries of the coronary artery tree,
detecting, by at least one of the at least one first evaluation algorithm, a coronary lumen surrounding the centerlines of the coronary arteries, and
classifying the coronary arteries of the coronary artery tree into segments for labelling by at least one of the at least one first evaluation algorithm according to at least one of a defined classification scheme or a user-selectable classification scheme of the coronary artery tree,
such that the at least one first evaluation data set describes, for each point in the coronary artery tree, a segment to which the point belongs, a local course of the segment, and a local shape of the segment;

determining at least one second evaluation data set describing at least one local medical feature in the anatomical structure using at least one second evaluation algorithm and entering the at least one second evaluation data set into the evaluation database;

determining the at least one evaluation information by applying inference rules of a rule set, wherein each inference rule derives at least one result evaluation data set from at least one input evaluation data sets and wherein the evaluation database is augmented by adding the result evaluation data sets for each rule application linked to the respective input evaluation data sets in the evaluation database; and outputting an interactive presentation comprising information from at least a part of the evaluation data sets of the evaluation database, wherein an initially displayed interactive presentation comprises at least one of the at least one evaluation information and, when a user interaction command related to at least one chosen result evaluation data set is received, updating the interactive presentation to include information of at least one input evaluation data set from which the chosen result evaluation data set is derived, wherein during the preprocessing the cardiac-gated coronary computed tomography angiography scan is split into several image data sets according to multiple phases of a heart cycle, at least one of the image data set of a defined heart phase is selected for evaluation or at least one of the image data set or a subset of the at least one image data set best meeting requirements of at least one of the at least one first evaluation algorithm or the at least one second evaluation algorithm is forwarded to a respective at least one of the at least one first evaluation algorithm or the at least one second evaluation algorithm, and the evaluation information comprises at least one atherosclerotic disease-related score and at least one calcium score for the patient.

16. An evaluation system for evaluating at least one image data set of an imaging region of a patient to determine at least one evaluation information describing at least one medical condition in an anatomical structure of the imaging region, wherein the evaluation system comprises:

a storage device configured to store an evaluation database and a rule set; and processing circuitry configured to execute computer-readable instructions to cause the evaluation system to, receive and preprocess the at least one image data set, the at least one image data set including at least one cardiac-gated coronary computed tomography angiography scan and at least one calcium scoring computed tomography scan, segment and label the anatomical structure using at least one first evaluation algorithm to generate at least one first evaluation data set and determine at least one second evaluation data set describing at least one local medical feature in the anatomical structure using at least one second evaluation algorithm, wherein the at least one first evaluation data set and the at least one second evaluation data set are entered into the evaluation database, the anatomical structure being a coronary artery tree and the segmenting and labelling including detecting, by at least one of the at least one first evaluation algorithm, centerlines of coronary arteries of the coronary artery tree, detecting, by at least one of the at least one first evaluation algorithm, a coronary lumen surrounding the centerlines of the coronary arteries, and classifying the coronary arteries of the coronary artery tree into segments for labelling by at least one of the at least one first evaluation algorithm according to at least one of a defined classification scheme or a user-selectable classification scheme of the coronary artery tree, such that the at least one first evaluation data set describes, for each point in the coronary artery tree, a segment to which the point belongs, a local course of the segment, and a local shape of the segment, determine the at least one evaluation information by applying inference rules of the rule set, wherein each inference rule derives at least one result evaluation data set from at least one input evaluation data set, wherein the evaluation database is augmented by adding the result evaluation data sets for each rule application linked to the respective input evaluation data sets in the evaluation database, and output an interactive presentation comprising in-formation from at least a part of the evaluation data sets of the evaluation database, wherein an initially displayed interactive presentation comprises at least one of the at least one evaluation information and the user interface is adapted to receive a user interaction command related to at least one chosen result evaluation data set and to update the interactive presentation to include information of at least one input evaluation data set from which the chosen result evaluation data set is derived, wherein during the preprocessing the cardiac-gated coronary computed tomography angiography scan is split into several image data sets according to multiple phases of a heart cycle, at least one of the image data set of a defined heart phase is selected for evaluation or at least one of the image data set or a subset of the at least one image data set best meeting requirements of at least one of the at least one first evaluation algorithm or the at least one second evaluation algorithm is forwarded to a respective at least one of the at least one first evaluation algorithm or the at least one second evaluation algorithm, and the evaluation information comprises at least one atherosclerotic disease-related score and at least one calcium score for the patient.

* * * * *